(12) United States Patent
Barber et al.

(10) Patent No.: US 8,598,123 B2
(45) Date of Patent: Dec. 3, 2013

(54) PEPTIDE ANALOGUES

(75) Inventors: Christopher Gordon Barber, Sandwich (GB); Dafydd Rhys Owen, Sandwich (GB); Lisa Rosemary Thompson, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/606,519

(22) Filed: Sep. 7, 2012

(65) Prior Publication Data

US 2012/0329724 A1 Dec. 27, 2012

Related U.S. Application Data

(63) Continuation of application No. 13/034,155, filed on Feb. 24, 2011.

(60) Provisional application No. 61/307,993, filed on Feb. 25, 2010.

(51) Int. Cl.
*A61K 38/05* (2006.01)
*A61P 25/04* (2006.01)

(52) U.S. Cl.
USPC ............ 514/18.4; 514/18.3; 514/21.91

(58) Field of Classification Search
None
See application file for complete search history.

(56) References Cited

U.S. PATENT DOCUMENTS

| 5,663,295 | A | 9/1997 | Moreau et al. ............ 530/330 |
| 6,114,310 | A | 9/2000 | Chamberland et al. | |

FOREIGN PATENT DOCUMENTS

| WO | WO9731940 | 9/1997 | ............ C07K 5/065 |
| WO | WO 9850421 A1 * | 11/1998 | ............ C07K 5/087 |

OTHER PUBLICATIONS

Shang et al, Design, synthesis and SAR studies of tripeptide analogs with the scaffold 3-phenylpropane-1,2-diamine as aminopeptidase N/CD13 inhibitors. Bioorganic & Medicinal Chemistry, 2009, 17, pp. 2775-2784, available online Feb. 24, 2009.*
Pitzele, et al., Journal of Medicinal Chemistry, vol. 37(7), pp. 888-896 (1994).
Dardonville, et al., "Synthesis and pharmacological studies of new hybrid derivatives of fentanyl active at the μ-opioid receptor and I2-imidazoline binding sites", Bioorganic & Medicinal Chemistry, vol. 14, pp. 6570-6580 (2006).
Schiller, et al., "Synthesis and in vitro opioid actvivity proviles of DALDA analogues", Eur. J. Med. Chem., vol. 35, pp. 895-901 (2000).
Szeto, et al., "In Vivo Pharmacokinetics of Selective μ-Opioid Peptide Agonists", JPET, vol. 298(1), pp. 57-61 (2001).
Bajusz, et al., "Further Enhancement of Analgesic Activity: Enkephalin Analogs with Terminal Guanidino Group", FEBS Letters, vol. 110(1), pp. 85-87 (1980).
Ogawa, et al., "Synthesis and in vivo Structure-Activity Relationships (SAR) of Orally-Active Analgesic Peptide, Nα-Amidino-Tyr-D-Arg-Phe-MEβAla-OH (ADAMB)", Peptide Science 2001, pp. 101-104 (2001).
Konopinska, "Proctolin—A Natural Insect Neuropeptide", Polish J. Chem., vol. 68(7), pp. 1437-1439 (1994).
Fanciulli, et al., "Effect of exogenous growth hormone administration on endogenous growth hormone secretion induced by a met-enkephalin analog", Eur. J. Endocrin., vol. 134, pp. 73-76 (1996).
Ogawa, et al., "Synthesis and Structure-Activity Relationships of an Orally Available and Long-Acting Analgesic Peptide Na-Amidino-Tyr-D-Arg-Phe-MeβAla-OH (ADAMB)", J. Med. Chem., vol. 45, pp. 5081-5089 (2002).
Ogawa, et al., "Structure-Activity Relationships (SAR) of [D-Arg2]Dermorphin(1--4)Analogues, Nα-Amidino-Tyr-D-Arg-Phe-X1", Chem. Pharm. Bull., vol. 50(6), pp. 771-780 (2002).
Dankwardt, et al., "Nonpeptide Bradykinin Antagonist Analogs Based on a Model of a Sterling-Winthrop Nonpeptide Bradykinin Antagonist Overlapped with Cyclic Hexapeptide Bradykinin Antagonist Peptides", Bioorg. Med. Chem. Letters., vol. 7(14), pp. 1921-1926 (1997).
Salvino, et al., "Structure Activity Relationships of Non-Peptide Bradykinin B2 Receptor Antagonists", Bioorg. & Med. Chem. Letters, vol. 5(4), pp. 357-362 (1995).
Kharkevich, et al., "Opioid ligands with extraordinarily high μ-selectivity: dermorphin tetrapeptides containing thymine-modified alanine residues", FEBS Letters, vol. 351, pp. 308-310(1994).
Hardy, et al., "Peripherally Acting Ankephalin Analogues. 2. Polar Tri- and Tetrapeptides", J. Med. Chem., vol. 32, pp. 1108-1118 (1989).
Hardy, et al., "Peripherally Acting Enkephalin Analogues. 1. Polar Pentapeptides", J. Med. Chem., vol. 31, pp. 960-966 (1988).
Marastoni, et al., "Synthesis and Activity Profiles of New Dermorphin-(1-4) Peptide Analogues", J. Med. Chem., vol. 30, pp. 1538-1542 (1987).
Salvadori, et al., "Synthesis and Opioid Activity of Dermorphin Tetrapeptides Bearing D-Methionine S-Oxide at Postition 2", J. Med. Chem., vol. 29, pp. 889-894 (1986).
Ronai, et al., "Enkephalin-Like Character and Analgesia", Eur. J. Pharmacol., vol. 69, pp. 263-271 (1981).
Velu, et al., "Antibacterial Nicotinamide Adenine Dinucleotide Synthetase Inhibitors: Amide- and Ether-Linked Tethered Dimers with α-Amino Acid End Groups", J. Med. Chem., vol. 50, pp. 2612-2621 (2007).
Liu, et al., "Differential cardiovascular effects of synthetic peptides derived from endomorphin-1 in anesthetized rats", Peptides, vol. 29, pp. 1048-1056 (2008).
Mizoguchi, et al., "Involvement of endogenous opioid peptides in the antinociception induced by the novel dermorphin tetrapeptide analog amidino-TAPA", Eur. J. Pharmacol., vol. 560, pp. 150-159 (2007).

(Continued)

Primary Examiner — Julie Ha
Assistant Examiner — Li Ni Komatsu
(74) Attorney, Agent, or Firm — A Dean Olson

(57) ABSTRACT

The present invention relates to compounds of Formula (I)

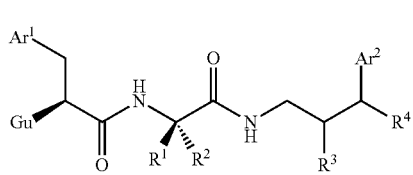

and their pharmaceutically acceptable salts, wherein the substituents are as described herein, and their use in medicine, in particular as opioid agonists.

3 Claims, No Drawings

(56) References Cited

OTHER PUBLICATIONS

Liu, et al., "Utilization of Combined Chemical Modifications to Enhance the Blood-Brain Barrier Permeability and Pharmacological Activity of Endomorphin-1", JPET, vol. 319(1), pp. 308-316 (2006).

Suhs, et al., "Synthesis of Functionalized Guanidino Amino Acids", Chemistry—a European Journal, vol. 12, pp. 8150-8157 (2006).

Wolin, et al., "Novel glycine transporter type-2 reuptake inhibitors. Part 1: α-amino acid derivatives", Bioorg. Med. Chem., vol. 12, pp. 4477-4492 (2004).

Deguchi, et al., "Blood-Brain Barrier Permeability of Novel [D-Arg2]Dermorphin (1-4) Analogs: Transport Property Is Related to the Slow Onset of Antinociceptive Activity in the Central Nervous System", JPET, vol. 310(1), pp. 177-184 (2004).

Genco, et al., "Antimicrobial activity of magainin analogues against anaerobic oral pathogens", International J. Antimicrobial Agents, vol. 21, pp. 75-78 (2003).

Salvadori, et al., "Synthesis and Opioid Activity of [Sar4]Dermorphin-Tetrapeptide Analogues", Hoppe-Seyler's Z. Physiol. Chem., vol. 365, pp. 1199-1206 (1984).

Castiglione, "Structure Activity Relationships in Dermorphin-Like Peptides", Highlights in Receptor Chemistry, Elsevier Science Publishers, pp. 149-168 (1984).

Salvadori, et al., "Synthesis and pharmacological activity of dermorphin tetrapeptide-analogs", Eur. J. Med. Chem.—Chim. Ther., vol. 1983-18(6), pp. 489-493 (1983).

Sarto, et al., "Opioid Peptides. Analgesic Activity of Potent Dermorphin Tetrapeptides", Farmaco Edizione Scientifica, pp. 647-652 (1983).

Tomatis, et al., "Opioid Activity of Synthetic 'Small Dermorphins'", Peptides, pp. 495-499 (1982).

Salvatori, et al., "Opioid Peptides. Structure-Activity Relationships in Dermorphin Tetrapeptides", Il Farmaco Ed. Sc., vol. 37(8), pp. 514-518 (1982).

Okayama, et al., "Exploration of Orally-Available and Long-Acting Opioid Peptides", Peptide Science, T. Yamada (Ed.), The Japanese Peptide Society, pp. 69-72 (2003).

Giusti, et al., "The effect of a met-enkephalin analogue on growth hormone, prolactin, gonadotropins, cortisol and thyroid stimulating hormone in healthy elderly men", Acta Endocrinologica, vol. 127, pp. 205-209 (1992).

Howlett, et al., "Lack of Modulation of the Adrenocortical Response to ACTH by an Opioid Peptide", Horm. Metab. Res., vol. 23, pp. 341-343 (1991).

Konopinska, et al., "Role of guanidine group at the N-terminal proctolin chain in cardioexcitatory effects in insects", Int. J. Peptide Protein Res., vol. 35, pp. 12-16 (1990).

Delitala, et al., "Opioids Stimulate Growth Hormone (GH) Release in Man Independently of GH-Releasing Hormone", J. Clin. Endocrin. Metab., vol. 69(2), pp. 356-358 (1989).

Borges, et al., "Opioid peptides do not modulate atrial natriuretic peptide or aldosterone release under basal conditions in man", J. Endocrin., vol. 116, pp. 313-317 (1988).

Cervini, et al., "Antinociceptive and Other Opioid Effects of a New Series of Dermorphin Analogues After Subcutaneous Administration in the Rat", Peptides, vol. 6, pp. 433-437 (1985).

Salvadori, et al., "Synthetic Tetrapeptides Related to Dermorphin: Potent Long Lasting Analgesic Action Following subcutaneous Administration", Peptides, vol. 6(3), pp. 127-129 (1985).

Marton, et al., "Effects of Synthetic Enkephalin Analogs on the Plasma Acth, Gh and PRL Level in Rats", Neuropeptides, Neurotransmitters and Regulation of Endocrine Processes, Neurohumoral Mech. pp. 303-307 (Meeting Date: 1982).

Kari, et al., "Structure-activity relationship studies of dialkylamine derivatives exhibiting wide spectrum antimicrobial activities", Frontiers of Peptide Science, Proceedings of American Peptide Symposium (15th) Jun. 14-19, 1997, pp. 196-197.

* cited by examiner

PEPTIDE ANALOGUES

This application is a continuation of U.S. application Ser. No. 13/034,155 filed on Feb. 24, 2011, which claims priority from U.S. Provisional Application No. 61/307,993 filed Feb. 25, 2010.

The invention described herein relates to peptide analogue compounds and the pharmaceutically acceptable salts of such compounds. The invention also relates to the processes for the preparation of the compounds, compositions containing the compounds, and the uses of such compounds and salts in treating diseases or conditions associated with opioid activity. More specifically the invention relates to the compounds and their salts useful as opioid agonists.

BACKGROUND

The opioid receptor family, consisting of μ-, δ- and κ-receptors, is a member of the rhodopsin subfamily in the superfamily of G-protein coupled receptors (GPCRs). These receptors share extensive structural and sequence homology (~60% amino acid identity) but recognise structurally diverse ligands comprising exogenous opiates, endogenous peptides and synthetic peptidic and non-peptidic ligands (Waldhoer et al., Annu. Rev. Biochem (2004) 73: 953-990). Opiates e.g. morphine and synthetic opioids e.g. fentanyl, acting through their activity at the μ-opioid receptor are some of the most potent analgesic drugs for moderate to severe pain conditions. However, for chronic pain conditions, their widespread use is limited by side effects such as constipation, respiratory depression, nausea, sedation, physical dependence and the potential for addiction. Opioid receptors are widely expressed in the central nervous system (CNS) and periphery of many species including man. Opioid receptors have been localised on peripheral processes of sensory neurones in animals and humans (Stein et al., 2003). Most opiates and opioids mediate their analgesic effects via peripheral, spinal and supraspinal receptors. However recent preclinical and clinical studies, using either local administration or compounds with special physicochemical and/or pharmacokinetic properties to restrict their action to the periphery, suggest that analgesia can be achieved via peripheral μ-opioid receptors (MORs) alone (Bileviciute-Ljungar et al., J. Pharmacol. Exp. Ther. (2006) 317: 220-227; Gordon et al., Drug disc. Today: Ther. Strat. (2009) in press; He et al., J. Pain (2009) 10: 369-379; Koppert et al., Anesth Analg (1999) 88: 117-122; Oeltjenbruns and Schafer, Curr. Pain Headache Reports 2005; 9: 36-44; Stein et al., Nat. Med. (2003) 9: 1003-1008; Stein and Lang, Curr. Opin. Pharmacol. (2009) 9: 1-6; Wenk et al., J. Neurophysiol. (2006) 95: 2083-2097). In general, efficacy is achieved under conditions of ongoing inflammation. This is consistent with the observation of increased primary afferent MORs in inflammatory models of pain and with the expression of MORs on inflammation-attracted immune cells. Frakefamide, a synthetic μ-opioid receptor agonist demonstrated efficacy in a dental pain study (Becktor et al., abstract from 2002 World Congress on Pain) at doses that did not elicit respiratory depression (Österlund Modalen et al., abstract from 2002 World Congress on Pain; Österlund Modalen et al., 2005; Anesth Analg, 100: 713-717). Synthetic compounds acting specifically through peripheral μ-opioid receptors provide the potential to effectively manage pain without the centrally-mediated adverse effects of drugs like morphine, e.g. Current Pharmaceutical Design, 2004 (10), 743-757; Ther Clin Risk Manag. 2005 December; 1(4): 279-297.

Replacement of Tyrosine with dimethylTyrosine is described in Bioorganic & Medicinal Chemistry Letters 17 (2007) 2043-2046, European Journal of Pharmacology, Volume 302, Issues 1-3, 29 Apr. 1996, Pages 37-42.

Various peptides and analogues thereof with biological activity, including some with opioid activity, are disclosed in:
Schiler et al in Eur. J. Med. Chem. 35 (2000) 895-901;
Szeto et al, JPET 298:57-61, 2001;
Bajusz et al, FEBS Letters January 1980, 110(1), 85-87
Ogawa et al, Peptide Science 2001, 101-104;
Konopinska, Polish J. Chem (1994), 68(7) 1437-9;
Fancioulli et al, Eur J Endocrinology (1996) 134: 73-76;
Giusti et al, Acta Endocrinologica (1992) 127: 205-209;
Howlett et al, Horm. Metab. Res. 23 (1991) 341-343;
Konopinska, Int. J. Peptide Protein Res. 35, 1990, 12-16;
Delitala et al, J. Clin. Endocrinology and Metabolism (1989), 69(2), 356-358;
Borges et al, J. Endocr. (1988) 116, 313-317;
Marastoni et al, II Farmaco—Ed. Sc. vol 42 fasc 2, 125-131;
Pastore et al, Peptides—Structures and Function, Proceedings of the 9$^{th}$ American Peptide Symposium 529-532;
Salvadori et al, Peptides, 6(Suppl 3), 1985, 127-129;
Cervinin et al, Peptides, vol 6, 1985, 433-437;
Marton et al, Neurohumoral Mech (1983) meeting date 1982, 303-307;
Salvadori et al, Hoppe-Seyler's Z. Physiol. Chem. Bd 365, S. 1199-1206, October 1984;
Castiglione, Highlights in Receptor Chemistry 1984 (publ. Elsevier), 149-168;
Salvadori et al, Eur J Med Chem Chim Ther 1983-18, no. 6, 489-493;
Sarto et al, Farmaco Ed. Sc. (1983) 647-652;
Tomatis et al, Peptides 1982, 495-499;
Salvadori et al, II Farmaco—Ed. Sc. 37(fasc 8) 514-518;
Hermann et al, Adv. Physiol. Sci, vol 14. Endocrinology, Neuroendocrinology, Neuropeptides—II, 333-337;
Ronai et al, Eur. J. Pharmacology 69 (1981) 263-271;
Okayama et al, Peptide Science 2002, Japanese Peptide Society, 69-72;
Salvadori et al, J. Med. Chem, 1986, 29, 889-894;
Marastoni et al, J. Med. Chem, 1987, 30, 1538-1542;
Castiglione-Morelli et al, J. Med. Chem, 1987, 30, 2067-2073;
Hardy et al, J. Med. Chem, 1988, 31, 960-966;
Hardy et al, J. Med. Chem, 1989, 32, 1108-1118;
Kharkevich et al, FEBS Letters 351 (1994) 308-301;
Salvino et al, Bioorganic & Medicinal Chemistry Letters 5(4) 357-362 (1995);
Dankwardt et al, Bioorganic & Medicinal Chemistry Letters 7(14) 1921-1926 (1997);
Ogawa et al, Chem Pharm Bull 50(6) 771-780 (2002);
Ogawa et al, J. Med. Chem., 2002, 45, 5081-5089;
Genco et al, Int. J. Antimicrobial Agents 21 (2003) 75-78;
Deguchi et al, JPET 310:177-184 (2004);
Wolin et al, Bioorganic & Medicinal Chemistry, 12 (2004) 4477-4492;
Liu et al, JPET 319:308-316 (2006);
Suhs et al, Chem. Eur. J. 2006, 12, 8150-8157;
Mizoguchi et al, Eur, J. Pharmacology 560 (2007) 150-159;
Liu et al, Peptides 29 (2008) 1048-1056;
Velu et al, J. Med. Chem. 2007, 50, 2612-2621;
and Chamberland et al, U.S. Pat. No. 6,114,310.

There is a need to provide new opioid receptor agonists that are good drug candidates. In particular, compounds should preferably bind potently to the μ-opioid receptor whilst showing little affinity for other receptors and show functional activity as μ-opioid receptor agonists. They should preferably be well absorbed from the gastrointestinal tract, and/or be injectable directly into the bloodstream, muscle, or subcutaneously, and/or be metabolically stable and possess favourable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will exist in a physical form that is stable, non-hygroscopic and easily formulated.

SUMMARY

The present invention relates to compounds of the Formula I:

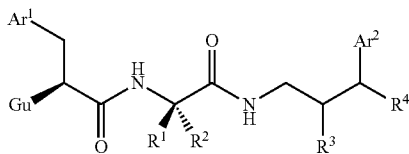

wherein $Ar^1$ is phenyl optionally substituted by one or more substituents independently selected from OH, $C_{1-3}$ alkyl and halogen, or $Ar^1$ is phenyl fused to a 5- or 6-membered heterocycle optionally substituted by one or more substituents independently selected from halogen, OH, and =O, $Ar^2$ is phenyl optionally substituted by one or more substituents independently selected from OH, $C_{1-3}$ alkyl and halogen, or $Ar^2$ is phenyl fused to a 5- or 6-membered heterocycle optionally substituted by one or more substituents independently selected from halogen, OH, and =O, Gu is guanidinyl optionally substituted by up to 4 substituents independently selected from $C_{1-3}$ alkyl (or a tautomeric form thereof), $R^1$ is independently H or $C_{1-5}$ alkyl optionally substituted by Y, where Y is halogen, $S(O)_m$—$(C_{1-3}$ alkyl), $CO_2$—$R^5$ or Gu, where $R^5$ is H or $C_{1-6}$ alkyl, and m is 0, 1 or 2, $R^2$ is independently H or $C_{1-3}$ alkyl, or $R^1$ and $R^2$ together with the carbon atom to which they are attached can be a cyclopropyl group, one of $R^3$ and $R^4$ is H and the other is Q where Q is H, $NH_2$, $NHC(O)(C_{1-6}$ alkyl), Gu, $NHC(O)(CH_2)_n NH2$, $NHC(O)(CH_2)_n Gu$, or $(CH_2)_n Gu$, where n is 1, 2, 3, 4 or 5, or a pharmaceutically acceptable salt thereof.

The invention is also directed to pharmaceutical compositions comprising a therapeutically effective amount of a compound of formula I herein, or a pharmaceutically acceptable salt thereof, and a pharmaceutically acceptable carrier.

The invention is also directed to a method of treating a disease or condition indicated for treatment with an opioid receptor agonist, particularly a μ-opioid receptor agonist, in a subject, by administering to a subject in need thereof a therapeutically effective amount of one or more of the compounds herein, or a pharmaceutically acceptable salt thereof.

Other aspects of the invention will be apparent from the remaining description and claims.

Preferably, the compounds of the present invention are potent agonists at the μ-opioid receptor, and have a suitable PK profile to enable once daily dosing. Particularly preferably, the compounds of the present invention have physical properties that minimise penetration into the CNS. Various references suggests that CNS penetration can be restricted through appropriate physiochemical properties such as lipophilicity, number of H-bond donors, polar surface area, number of charged centres (see e.g. K. M. M. Doan THE JOURNAL OF PHARMACOLOGY AND EXPERIMENTAL THERAPEUTICS 2002, Vol. 303 (3) 1029-1037 and L. Di, Expert Opinion on Drug Discovery June 2008, Vol. 3, No. 6: 677-687).

The compounds of the present invention are potentially useful in the treatment of a range of disorders where an opioid agonist is indicated, particularly pain indications. Depending on the disease and condition of the patient, the term "treatment" as used herein may include one or more of curative, palliative and prophylactic treatment.

According to the invention a compound of the present invention may be used to treat any physiological pain such as inflammatory pain, nociceptive pain, neuropathic pain, acute pain, chronic pain, musculo-skeletal pain, on-going pain, central pain, heart and vascular pain, head pain, orofacial pain. Other pain conditions which may be treated include intense acute pain and chronic pain conditions which may involve the same pain pathways driven by pathophysiological processes and as such cease to provide a protective mechanism and instead contribute to debilitating symptoms associated with a wide range of disease states.

Pain is a feature of many trauma and disease states. When a substantial injury, via disease or trauma, to body tissue occurs the characteristics of nociceptor activation are altered, this leads to hypersensitivity at the site of damage and in nearby normal tissue.

In acute pain the sensitivity returns to normal once the injury has healed. However, in many chronic pain states, the hypersensitivity far outlasts the healing process and is normally due to nervous system injury due to maladaptation of the afferent fibres (Woolf & Salter 2000 Science 288: 1765-1768). Clinical pain is present when discomfort and abnormal sensitivity feature among the patient's symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13-44). Pain can be divided into a number of different areas because of differing pathophysiology, these include nociceptive, inflammatory, neuropathic pain among others. It should be noted that some types of pain have multiple aetiologies and thus can be classified in more than one area, e.g. Back pain, Cancer pain have both nociceptive and neuropathic components.

Nociceptive Pain

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13-44). The activation of nociceptors activates two types of afferent nerve fibres. Myelinated A-delta fibres transmit rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertabral discs or abnormalities of the lumbar facet joints, sacroiliac joints, paraspinal muscles or the posterior longitudinal ligament.

Neuropathic Pain

According to the invention a compound of the present invention can potentially be used to treat neuropathic pain and the symptoms of neuropathic pain including hyperalgesia, allodynia and ongoing pain. Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959-1964). The symptoms of neuropathic pain are difficult to treat, as they are often heterogeneous even between patients with the same disease (Woolf & Decosterd 1999 Pain Supp. 6: S141-S147; Woolf and Mannion 1999 Lancet 353: 1959-1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

Intense Acute Pain and Chronic Pain

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765-1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) exaggerated pain responses to noxious stimuli (hyperalgesia); 3) pain is produced by normally innocuous stimuli (allodynia) (Meyer et al., 1994 Textbook of Pain 13-44). Although patients with back pain, arthritis pain, CNS trauma, or neuropathic pain may have similar symptoms, the underlying mechanisms are different and, therefore, may require different treatment strategies.

Chronic Pain

Chronic pain comprises one or more of, chronic nociceptive pain, chronic neuropathic pain, chronic inflammatory pain, breakthrough pain, persistent pain hyperalgesia, allodynia, central sensitisation, peripheral sensitisation, disinhibition and augmented facilitation.

Chronic pain includes cancer pain, e.g. cancer pain arising from malignancy, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumour s, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumours, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukaemia, primary or secondary bone cancer, tumours that metastasize to the bone, tumours infiltrating the nerve and hollow viscus, tumours near neural structures. Cancer pain also comprises visceral pain, e.g. visceral pain which arises from pancreatic cancer and/or metastases in the abdomen, somatic pain, e.g. somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

Inflammatory Pain

Inflammatory conditions include acute inflammation, persistent acute inflammation, chronic inflammation, and combined acute and chronic inflammation.

Inflammatory pain includes acute inflammatory pain and/or chronic inflammatory pain wherein the chronic inflammatory pain can be pain involving both peripheral and central sensitisation and/or mixed etiology pain involving both inflammatory pain and neuropathic pain or nociceptive pain components. Inflammatory pain also comprises hyperalgesia, e.g. primary and/or secondary hyperalgesia. Additionally or alternatively the inflammatory pain can include allodynia. Inflammatory pain also comprises pain that persists beyond resolution of an underlying disorder or inflammatory condition or healing of an injury.

Inflammatory pain is pain resulting an inflammatory condition. e.g. in response to acute tissue injury due to trauma, disease e.g. an inflammatory disease, immune reaction, the presence of foreign substances, chemicals or infective particles for example micro-organisms. Inflammatory conditions can be either acute or chronic inflammation or both. Inflammatory pain can result from an inflammatory condition due to an inflammatory disease such as inflammatory joint diseases, inflammatory connective tissue diseases, inflammatory autoimmune diseases, inflammatory myopathies, inflammatory digestive system diseases, inflammatory air way diseases, cellular immune inflammation diseases, hypersensitivities and allergies, vasular inflammation diseases, non-immune inflammatory disease, synovitis, villonodular synovitis, arthralgias, ankylosing spondylitis, spondyloarthritis, spondyloarthropathy, gout, Pagets disease, particular disorders such as bursitis, rheumatoid disease, rheumatoid arthritis and osteoarthritis, rheumatoid arthritis or osteoarthritis. Rheumatoid arthritis in particular, represents ongoing inflammation associated with severe pain. Arthritic pain is a form of inflammatory pain and arises from inflammation in a joint which causes both peripheral sensitization and central sensitization. Under inflammatory conditions the nociceptive system is activated by normally innocuous and nonpainful mechanical stimuli. Additionally when the joint is at rest pain is present and appears as spontaneous pain and hyperalgesia (augmented pain response on noxious stimulation and pain on normally nonpainful stimulation). Inflammatory processes in peripheral tissues lead to central sensitization in the spinal cord, which contributes to hyperalgesia and allodynia typically associated with inflammatory pain. Other types of inflammatory pain include inflammatory bowel diseases (IBD).

Other Types of Pain

Other types of pain include but are not limited to:

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis;

Central pain or 'thalamic pain' as defined by pain caused by lesion or dysfunction of the nervous system including but not limited to central post-stroke pain, multiple sclerosis, spinal cord injury, Parkinson's disease and epilepsy;

Heart and vascular pain including but not limited to angina, myocardial infarction, mitral stenosis, pericarditis, Raynaud's phenomenon, scleroderma, scleredoma, skeletal muscle ischemia;

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis;

Head pain including but not limited to migraine, migraine with aura, migraine without aura cluster headache, tension-type headache. Orofacial pain including but not limited to dental pain, temporomandibular myofascial pain, tinnitus, hot flushes, restless leg syndrome and blocking development of abuse potential. Further pain conditions may include, back pain, bursitis, dental pain, fibromyalgia or myofacial pain, menstrual pain, migraine, neuropathic pain (including painful diabetic neuropathy), pain associated with post-herpetic neuralgia, post-operative pain, referred pain, trigeminal neuralgia, visceral pain (including interstitial cystitis and IBS) and pain associated with AIDS, allodynia, burns, cancer, hyperalgesia, hypersensitisation, spinal trauma and/or degeneration and stroke.

Other conditions that may be treated with the compounds of the present invention include urogenital indications and others e.g. urinary incontinence, overactive bladder, emesis, cognitive disorders, anxiety, depression, sleeping disorders, eating disorders, movement disorders, glaucoma, psoriasis, multiple sclerosis, cerebrovascular disorders, brain injury, gastrointestinal disorders, hypertension, cardiovascular disease.

DETAILED DESCRIPTION

The present invention relates to compounds of the Formula I:

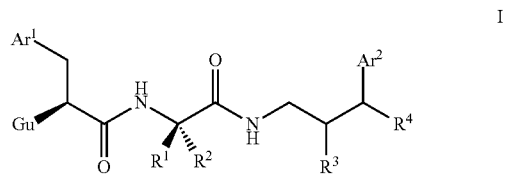

wherein $Ar^1$ is phenyl optionally substituted by one or more substituents independently selected from OH, $C_{1-3}$ alkyl and halogen, or $Ar^1$ is phenyl fused to a 5- or 6-membered heterocycle optionally substituted by one or more substituents independently selected from halogen, OH, and =O, $Ar^2$ is phenyl optionally substituted by one or more substituents independently selected from OH, $C_{1-3}$ alkyl and halogen, or $Ar^2$ is phenyl fused to a 5- or 6-membered heterocycle optionally substituted by one or more substituents independently selected from halogen, OH, and =O, Gu is guanidinyl (or a tautomeric form thereof) optionally substituted by up to 4 substituents independently selected from $C_{1-3}$ alkyl, $R^1$ is independently H or $C_{1-5}$ alkyl optionally substituted by Y, where Y is halogen, $S(O)_m$—($C_{1-3}$ alkyl), $CO_2$—$R^5$ or Gu, where $R^5$ is H or $C_{1-6}$ alkyl, and m is 0, 1 or 2, $R^2$ is H or $C_{1-3}$ alkyl, or $R^1$ and $R^2$ together with the carbon atom to which they are attached can be a cyclopropyl group, one of $R^3$ and $R^4$ is H and the other is Q where Q is H, $NH_2$, $NHC(O)(C_{1-6}$ alkyl), Gu, $NHC(O)(CH_2)_n NH2$, $NHC(O)(CH_2)_n Gu$, or $(CH_2)_n Gu$, where n is 1, 2, 3, 4 or 5, or a pharmaceutically acceptable salt thereof.

The invention is also directed to pharmaceutical compositions comprising a therapeutically effective amount of a compound of formula I herein, or a pharmaceutically acceptable salt thereof, and a pharmaceutically acceptable carrier.

The invention is also directed to a method of treating a disease or condition indicated for treatment with an opioid receptor agonist, particularly a µ-opioid receptor agonist, in a subject, by administering to a subject in need thereof a therapeutically effective amount of one or more of the compounds herein, or a pharmaceutically acceptable salt thereof.

Other aspects of the invention will be apparent from the remaining description and claims.

Preferably $Ar^1$ is phenyl optionally substituted by one or more substituents independently selected from OH and $C_{1-3}$ alkyl, or $Ar^1$ is phenyl fused to a 5- or 6-membered heterocycle optionally substituted by =O.

More preferably $Ar^1$ is 4-hydroxyphenyl, 2,6-dimethyl-4-hydroxyphenyl or benzoxazol-2-one-6-yl.

Most preferably $Ar^1$ is 2,6-dimethyl-4-hydroxyphenyl.

Preferably $Ar^2$ is phenyl optionally substituted by one or more substituents independently selected from OH and $C_{1-3}$ alkyl.

More preferably $Ar^2$ is 2,6-dimethyl-4-hydroxyphenyl or phenyl.

Most preferably $Ar^2$ is phenyl.

Preferably Gu is a guanidinyl optionally substituted by up to 4 methyl groups.

More preferably Gu is guanidinyl or tetramethylguanidinyl.

Most preferably Gu is guanidinyl.

Preferably $R^1$ is H or $C_{1-5}$ alkyl optionally substituted by Y, where Y is $S(O)_m$—($C_{1-3}$ alkyl) or $CO_2H$.

Preferably $R^1$ is $C_{1-5}$ alkyl optionally substituted by $S(O)CH_3$ or $CO_2H$.

More preferably $R^1$ is methyl, $(CH_2)_5CO_2H$ or $(CH_2)_2S(O)CH_3$.

Most preferably $R^1$ is methyl.

Preferably $R^2$ is H.

Preferably one of $R^3$ and $R^4$ is H and the other is Q where Q is H, $NH_2$, $NHC(O)CH_3$, guanidinyl, $NHC(O)CH_2 NH_2$, $NHC(O)CH_2$-guanidine, $NHC(O)CH_2 CH_2 NH_2$, $NHC(O)CH_2 CH_2$-guanidine or $CH_2$-guanidine.

More preferably $R^3$ is Q and $R^4$ is H.

Yet more preferably $R^3$ and $R^4$ are as follows:
$R^3$ is guanidinyl and $R^4$ is H;
$R^3$ is H and $R^4$ is H;
$R^3$ is $NHC(O)CH_3$ and $R^4$ is H; or
$R^3$ is $NH_2$ and $R^4$ is H.

Most preferably $R^3$ is guanidinyl and $R^4$ is H.

Preferably the stereochemistry of the $R^3$ group is as shown in formula Ia below.

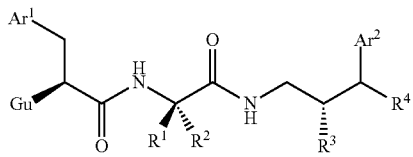

Ia

Preferable groups of compounds of formula I, and Ia, and their pharmaceutically acceptable salts are those wherein:
$Ar^1$ has the value of $Ar^1$ of any of the specific compounds mentioned below;
$Ar^2$ has the value of $Ar^2$ of any of the specific compounds mentioned below;
Gu has the value of Gu of any of the specific compounds mentioned below;
$R^1$ has the value of $R^1$ of any of the specific compounds mentioned below;
$R^2$ has the value of $R^2$ of any of the specific compounds mentioned below;
$R^3$ has the value of $R^3$ of any of the specific compounds mentioned below;
and/or
$R^4$ has the value of $R^4$ of any of the specific compounds mentioned below.

Preferred groups of compounds of formula I and Ia and their pharmaceutically acceptable salts are those wherein:
$Ar^1$ is 4-hydroxyphenyl, 2,6-dimethyl-4-hydroxyphenyl or benzoxazol-2-one-6-yl;
$Ar^2$ is 2,6-dimethyl-4-hydroxyphenyl or phenyl;
Gu is guanidinyl or tetramethylguanidinyl;
$R^1$ is methyl, $(CH_2)_5CO_2H$ or $(CH_2)_2S(O)CH_3$;

$R^2$ is H;
and $R^3$ and $R^4$ are as follows:
$R^3$ is guanidinyl and $R^4$ is H;
$R^3$ is H and $R^4$ is H;
$R^3$ is $NHC(O)CH_3$ and $R^4$ is H; or
$R^3$ is $NH_2$ and $R^4$ is H.

The most preferred compounds of formula I are those specifically mentioned in the Examples below, and their pharmaceutically acceptable salts.

"Guanidinyl" means the group below.

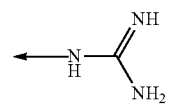

"Halogen" means a fluoro, chloro, bromo or iodo group;

"Alkyl" groups, containing the requisite number of carbon atoms, can be unbranched or branched. Examples of alkyl include methyl, ethyl, n-propyl, i-propyl, n-butyl, i-butyl, sec-butyl and t-butyl.

"5- to 6-membered heterocycle" can include 1, 2 or 3 heteroatoms independently selected from N, O and S, and can be fully saturated, partially unsaturated, or fully unsaturated. Examples preferably include oxazole, or imidazole, or triazole, but can also be selected from pyrrole, furan, thiophene, pyrazole, isoxazole, thiazole, isothiazole, dithiazole, furazan, oxadiazole, thiadiazole, tetrazole, pyridine, pyran, thipyran, diazine, oxazine, thiazine, dioxin, triazine, tetrazine, and any fully saturated and partially unsaturated analogues thereof.

"Pharmaceutically acceptable salts" of the compounds of formula I include the acid addition and base addition salts (including disalts, hemisalts, etc.) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base addition salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

The compounds of the invention include compounds of formula I and salts thereof as hereinbefore defined, polymorphs, and isomers thereof (including optical, geometric and tautomeric isomers) as hereinafter defined and isotopically-labelled compounds of formula I.

It is important to realise that all the compounds of the invention may exhibit tautomeric behaviour at one or more functional groups. It is to be understood from the definitions herein that where such groups are specified, each tautormeric form is also included.

Examples of groups which may exhibit tautomerism will be familiar to those skilled in the art and include:

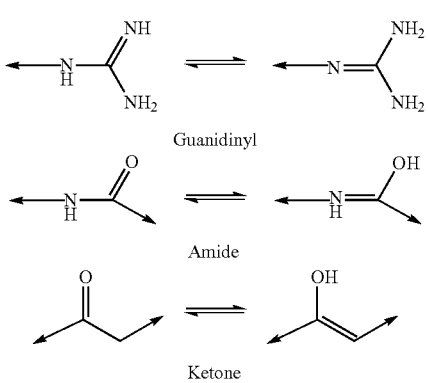

Guanidinyl

Amide

Ketone

Unless otherwise specified, compounds of formula (I) containing one or more asymmetric carbon atoms can exist as two or more stereoisomers.

It follows that a single compound may exhibit more than one type of isomerism.

Included within the scope of the claimed compounds of the present invention are all stereoisomers, geometric isomers and tautomeric forms of the compounds of formula (I), including compounds exhibiting more than one type of isomerism, and mixtures of one or more thereof. Also included are acid addition or base addition salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or other derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagents in place of the non-labelled reagent previously employed.

There are a number of methods by which compounds of the general formula I and their salts can be prepared which will be apparent to those skilled in the art, exemplified in the Preparations and Examples below. A primary amine can be converted to the corresponding guanidine either in a protected form, or directly in the absence of guanidine protection.

For example a free amine compound of formula INT1 (below) can be converted to the corresponding compound of formula (I) by reaction with a carboxamidine such as 3,5-dimethylpyrazol-1-carboxamidine.

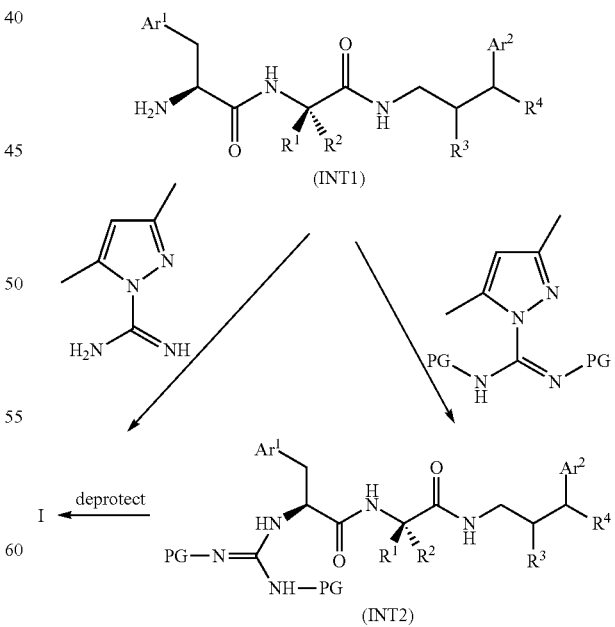

If more than one guanidine is present, they can be added simultaneously, or in sequence, or by combining fragments that each contain a guanidine in either a protected or unprotected form (an example of a protected product of this reaction is INT2 above (e.g. where "PG" is an appropriate protecting group such as Cbz—exemplified in the synthesis of Examples 1-9, or a Boc group—exemplified in the synthesis of Example 10, and relevant Preparations). Such intermediates can be constructed by assembling fragments through the formation of amide bonds from amines using standard bond coupling conditions such as those using mixed anhydrides or active esters of the relevant acid moiety. Appropriate protecting groups may be applied, such as those described in standard texts such as "Protecting Groups" P. J. Kocieński, ed. Thieme; "Protective Groups in Organic Synthesis" Theodora W. Greene ed. Wiley; etc. In particular, tert-butoxycarbonyl (Boc) amines and guanidines may be used and subsequently deprotected under acidic conditions using, for example, hydrogen chloride or trifluoroacetic acid in an organic co-solvent such as dioxan or dichloromethane. Similarly, benzyloxycarbonyl (Cbz) amines and guanidines may be used and subsequently deprotected under hydrogenolytic conditions using, for example, catalytic molecular hydrogenation or transfer hydrogenation protocols familiar to those skilled in the art.

Pharmaceutically acceptable salts of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention intended for pharmaceutical use may be administered alone or in combination with one or more other compounds of the invention or in combination with one or more other drug agent (or as any combination thereof). Generally, they will be administered as a formulation in association with one or more pharmaceutically acceptable excipients. The term "excipient" is used herein to describe any biologically inactive ingredient other than the compounds and salts of the invention. The choice of excipient will to a large extent depend on factors such as the particular mode of administration, the effect of the excipient on solubility and stability, and the nature of the dosage form. For example, a compound of the formula I, or a pharmaceutically acceptable salt or solvate thereof, as defined above, may be administered simultaneously (e.g. as a fixed dose combination), sequentially or separately in combination with one or more other drug agent.

Exemplary additional agents could be selected from one or more of:

- a Nav1.7 channel modulator, such as a compound disclosed in WO 2009/012242 or WO2010/079443;
- an alternative sodium channel modulator, such as a Nav1.3 modulator (e.g. as disclosed in WO02008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
- an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagoinsist;
- a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene)piperidene-1-carboxamide);
- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
- a muscarinic antagonist, e.g oxybutynin, tolterodine, propiverine, tropsium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5\text{-HT}_{1B/1D}$ agonist such as eletriptan, sumatriptan, naratriptan, zolmitriptan or rizatriptan;

a $5\text{-HT}_{2A}$ receptor antagonist such as R(+)-alpha-(2,3-dimethoxy-phenyl)-1-[2-(4-fluorophenylethyl)]-4-piperidinemethanol (MDL-100907);

a $5\text{-HT}_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504).

Pharmaceutical compositions suitable for the delivery of compounds and salts of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Compounds and salts of the invention intended for pharmaceutical use may be prepared and administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

Parenteral Administration

The compounds and salts of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) and salts used in the preparation of parenteral solutions may be increased by the use of appropriate formulation techniques, such as the incorporation of solubility-enhancing agents.

Formulations for parenteral administration may be formulated to be immediate and/or modified release. Thus, compounds and salts of the invention may be formulated as a solid, semi-solid, or thixotropic liquid for administration as an implanted depot providing modified release of the active compound. An example of such formulations include drug-coated stents.

Topical Administration

The compounds and salts of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated [see, for example, Finnin and Morgan, J Pharm Sci, 88 (10), 955-958 (October 1999).]

Other means of topical administration include delivery by electroporation, iontophoresis, phonophoresis, sonophoresis and microneedle or needle-free (e.g. Powderject™, Bioject™, etc.) injection.

Inhaled/Intranasal Administration

The compounds and salts of the invention may also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

A pressurised container, pump, spray, atomizer, or nebuliser may contain a solution or suspension of the compound(s) or salt(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound or salt of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound or salt of the invention per actuation and the actuation volume may vary from 1 µl to 100 µl. A typical formulation may comprise a compound of formula (I) or salt thereof, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by a prefilled capsule, blister or pocket or by a system that utilises a gravimetrically fed dosing chamber. Units in accordance with the invention are typically arranged to administer a metered dose or "puff" containing from 1 to 5000 µg of the compound or salt. The overall daily dose will typically be in the range 1 µg to 20 mg which may be administered in a single dose or, more usually, as divided doses throughout the day.

Rectal/Intravaginal Administration

The compounds and salts of the invention may be administered rectally or vaginally, for example, in the form of a suppository, pessary, or enema. Cocoa butter is a traditional suppository base, but various well known alternatives may be used as appropriate.

Ocular and Aural Administration

The compounds and salts of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid; a cellulosic polymer, for example, hydroxypropylmethylcellulose, hydroxyethylcellulose, or methyl cellulose; or a heteropolysaccharide polymer, for example, gelan gum, may be incorporated together with a preservative, such as benzalkonium chloride. Such formulations may also be delivered by iontophoresis.

Other Technologies

The compounds and salts of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the compounds and salts of the invention is typically in the range 0.1 mg to 200 mg depending, of course, on the mode of administration, preferred in the range 1 mg to 100 mg and more preferred in the range 1 mg to 50 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the above-mentioned therapeutic uses, the dosage administered will, of course, vary with the compound or salt employed, the mode of administration, the treatment desired and the disorder indicated. The total daily dosage of the compound of formula (I)/salt/solvate (active ingredient) will, generally, be in the range from 1 mg to 1 gram, preferably 1 mg to 250 mg, more preferably 10 mg to 100 mg. The total daily dose may be administered in single or divided doses. The present invention also encompasses sustained release compositions.

The pharmaceutical composition may, for example, be in a form suitable for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

For parenteral dosages, this may conveniently be prepared as a solution or as a dry powder requiring dissolution by a pharmacist, medical practitioner or the patient. It may be provided in a bottle or sterile syringe. For example it may be provided as a powder in a multicompartment syringe which allows the dry powder and solvent to be mixed just prior to administration (to aid long-term stability and storage). Syringes could be used which allow multiple doses to be administered from a single device.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

A composition of the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, (1978). Pharmaceutical compositions are preferably manufactured under GMP conditions.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The precise dosage administered of each active ingredient will vary depending upon any number of factors, including but not limited to, the type of animal and type of disease state being treated, the age of the animal, and the route(s) of administration.

The following non-limiting Preparations and Examples illustrate the preparation of compounds and salts of the present invention.

General Experimental

The Preparations and Examples that follow illustrate the invention but do not limit the invention in any way. All starting materials are available commercially or described in the literature. All temperatures are in ° C. Flash column chromatography was carried out using Merck silica gel 60 (9385). Thin layer chromatography (TLC) was carried out on Merck silica gel 60 plates (5729). "$R_f$" represents the distance travelled by a compound divided by the distance travelled by the solvent front on a TLC plate. Melting points were determined using a Gallenkamp MPD350 apparatus and are uncorrected. NMR was carried out using a Varian-Unity Inova 400 MHz NMR spectrometer or a Varian Mercury 400 MHz NMR spectrometer. Mass spectroscopy was carried out using a Finnigan Navigator single quadrupole electrospray mass spectrometer or a Finnigan aQa APCI mass spectrometer.

Where it is stated that compounds were prepared in the manner described for an earlier Preparation or Example, the skilled person will appreciate that reaction times, number of equivalents of reagents and reaction temperatures may be modified for each specific reaction, and that it may nevertheless be necessary or desirable to employ different work-up or purification conditions.

The invention is illustrated by the following non-limiting examples in which the following abbreviations and definitions are used:

APCI atmospheric pressure chemical ionisation mass spectrum
Arbocel filter agent
br broad
cbz benzyloxycarbonyl
δ chemical shift
d doublet
DCM dichloromethane
dd doublet of doublets
DMF N,N-dimethylformamide
EDC 1-(3-dimethylaminopropyl)-3-ethyl carbodiimide hydrochloride
ES electrospray ionisation
EtOH Ethanol HBTU O-(benzotriazol-1-yl)-N,N,N',N'-tetramethyluronium hexafluorophosphate
HOBt 1-hydroxybenzotriazole monohydrate
HPLC high pressure liquid chromatography
hrs hours
IBCF isobutylchloroformate
LRMS low resolution mass spectrum
m multiplet
Me methyl
MeOH Methanol
m/z mass spectrum peak
NMR nuclear magnetic resonance
NMM 4-methylmorpholine
psi pounds per square inch
q quartet
RM reaction mixture
rt room (ambient) temperature
Rt retention time
s singlet
SM starting material
soln. solution
t triplet
TFA trifluoroacetic acid
THF tetrahydrofuran
tlc thin layer chromatography For the avoidance of doubt, named compounds used herein have been named using ACD Labs Name Software v7.11™.

Where compounds are purified by HPLC, there are two methods used, shown below.

|  | Method a | Method b |
|---|---|---|
| Column | Sunfire C18 4.6 × 50 mm id column | Xterra 4.6 × 50 mm id column |
| Temperature | Ambient | Ambient |
| Mobile Phase A | 0.05% formic acid in water | 0.05% ammonia in water |
| Mobile Phase B | 0.05% formic acid in acetonitrile | 0.05% ammonia in acetonitrile |
| Gradient - Initial | 5% B | 5% B |
| Time 0 mins | 5% B | 5% B |
| Time 3 mins | 98% B | 98% B |
| Time 4 mins | 98% B | 98% B |
| Time 4.1 mins | 5% B | 5% B |
| Time 5 mins | 5% B | 5% B |
| Flow rate | 1.5 ml/min | 1.5 ml/min |
| Injection volume | 5 ul | 5 ul |

EXAMPLES

Example 1

N-[Amino(imino)methyl]-2,6-dimethyl-L-tyrosyl-N-[(2S)-2-{[amino(imino)methyl]amino}-3-phenylpropyl]-D-alaninamide

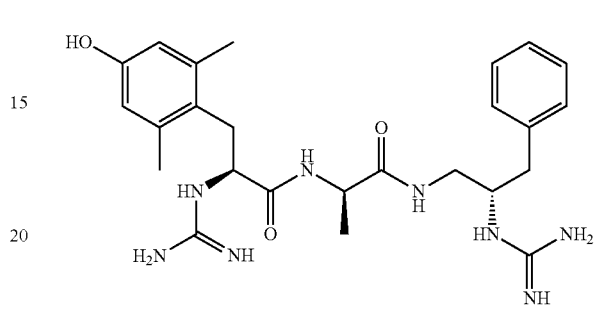

N-[(Z)-{[(benzyloxy)carbonyl]amino)}{[(benzyloxy)carbonyl]imino}methyl]-2,6-dimethyl-L-tyrosyl-N-[(2S)-2-{[(E)-{[(benzyloxy)carbonyl]amino}{[(benzyloxy)carbonyl]imino}methyl]amino}-3-phenylpropyl]-D-alaninamide from preparation 40 (138 mg, 0.134 mmol) was dissolved in methanol (2 mL) and 1.25M HCl in methanol (0.2 mL) was added followed by 10% Pd/C (80 mg, 0.75 mmol). The mixture was then hydrogenated at 50 psi (~345 kPa) and rt for 15 hrs. The reaction was filtered through a pad of Arbocel and the filtrate concentrated under reduced pressure. The residue was purified by column chromatography (silica, 10% MeOH in DCM as eluant increasing to DCM:MeOH:NH$_{3\,aq}$ 80:20:2 as eluant) to afford the title compound as a white solid in 29% yield, 19 mg. $^1$H NMR (400 MHz, MeOH-d4) δ: 1.18 (d, 3H), 1.26-1.42 (m, 1H), 2.66 (dd, 1H), 2.95-3.06 (m, 2H), 3.15-3.24 (m, 2H), 3.33-3.41 (m, 1H), 3.78-3.90 (m, 1H), 4.16-4.29 (m, 1H), 4.37-4.45 (m, 1H), 6.49 (s, 2H), 7.16-7.33 (m, 5H).

Examples 2-9 were similarly prepared according to the method described above for example 1, starting from the appropriate protected guanidine of formula 1.

| Ex. | Precursor | Structure | Conditions | Data |
|---|---|---|---|---|
| 2 | Prep. 41 | Mixture of epimers | 1.25M HCl in MeOH, MeOH, Pd/C, H$_2$, rt, 60 psi (~414 kPa) (0.054 mmol) Yield = 79% | $^1$H NMR (400 MHz, MeOH-d4)δ : 1.17 (d, 3H), 2.14-2.20 (m, 1H), 2.28 (s, 6H), 2.64-2.66 (m, 2H), 2.98-3.03 (m, 1H), 3.10-3.28 (m, 5H), 4.15-4.21 (m, 1H), 4.29-4.34 (m, 1H), 6.49 (s, 2H), 7.18-7.23 (m, 3H), 7.27-7.31 (m, 2H). LRMS APCI m/z 511 [MH]$^+$ |

| Ex. | Precursor | Structure | Conditions | Data |
|---|---|---|---|---|
| 3 | Prep. 51 | (structure) | 1.25M HCl in MeOH, MeOH, Pd/C, H₂, rt, 60 psi (~414 kPa) (0.073 mmol) Yield = 84% | ¹H NMR (400 MHz, MeOH-d4) δ: 1.07 (d, 3H), 2.28 (S, 6H), 2.69 (m, 1H), 2.80-3.22 (m, 17H), 3.80 (m, 1H), 4.13 (m, 2H), 6.51 (s, 2H), 7.20-7.37 (m, 5H). LRMS APCI m/z 553 [MH]⁺ |
| 4 | Prep. 43 | (structure) | 1.25M HCl in MeOH, MeOH, Pd/C, H₂, rt, 60 psi (~414 kPa) (0.348 mmol) Yield = 17% | ¹H NMR (400 MHz, MeOH-d4) δ: 1.33 (d, 3H), 2.67 (dd, 1H), 2.91 (dd, 1H), 3.01 (dd, 1H), 3.11 (dd, 1H), 3.32-3.41 (m, 2H), 3.82-3.86 (m, 1H), 4.27 (q, 1H), 4.40 (d, 1H), 6.73 (d, 2H), 7.07 (d, 2H), 7.22-7.29 (m, 5H). LRMS m/z 469 [MH]+ |
| 5 | Prep. 44 | (structure) | 1.25M HCl in MeOH, MeOH, Pd/C, H₂, rt, 60 psi (~414 kPa) (0.147 mmol) Yield = 76% | ¹H NMR (400 MHz, MeOH-d4) δ: 1.26 (d, 3H), 2.27 (s, 6H), 2.90 (m, 3H), 3.83 (q, 2H), 4.19 (m, 2H), 4.36 (m, 1H), 6.49 (br s, 2H), 7.23 (m, 6H), 7.68 (m, 1H), 7.93 (m, 1H), 8.10 (m, 1H). LC-MS Rt. 1.39; LRMS APCI m/z 554 [MH]⁺ |
| 6 | Prep. 45 | (structure) | 1.25M HCl in MeOH, MeOH, Pd/C, H₂, rt, 60 psi (~414 kPa) (0.082 mmol) Yield = 68% | ¹H NMR (400 MHz, MeOH-d4) δ: 1.15 (d, 3H), 2.28 (s, 6H), 2.32-2.50 (m, 2H), 2.80-2.85 (m, 1H), 2.97-3.02 (m, 1H), 3.13-3.41 (m, 4H), 4.16-4.24 (m, 2H), 4.34-4.38 (m, 1H), 6.48 (s, 2H), 7.14-7.26 (m, 5H). LRMS m/z 568 [MH]+ |

| Ex. | Precursor | Structure | Conditions | Data |
|---|---|---|---|---|
| 7 | Prep. 46 | 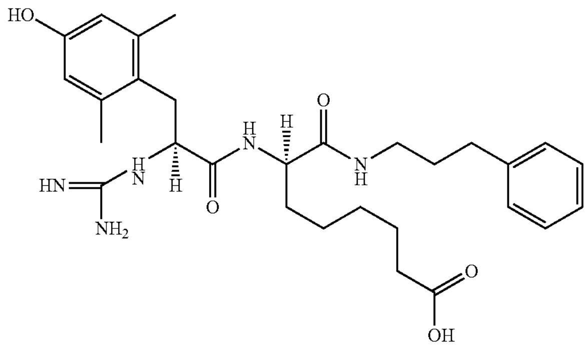 [SMILES: Cc1cc(O)cc(C)c1C[C@H](NC(=N)N)C(=O)N[C@H](CCCCCC(=O)O)C(=O)NCCCc1ccccc1] | Pd/C, H₂, EtOH, rt, 50 psi (~345 kPa) (0.062 mmol) Yield = 54% | 1H NMR (400 MHz, MeOH-d4) δ: 0.90 (m, 2H), 1.07 (m, 1H), 1.28 (m, 6H), 1.55 (m, 4H), 2.22 (m, 6H), 2.61 (m, 1H), 2.94 (m, 1H), 3.18 (m, 1H), 4.13 (m, 1H), 4.21 (m, 1H), 6.50 (br s, 2H), 7.19 (m, 5H). LRMS APCI m/z 540 [MH]⁺ |
| 8 | Prep. 47 | 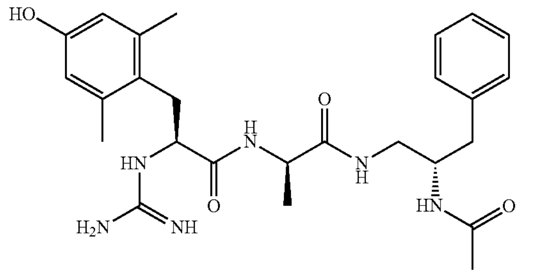 [SMILES: CC(=O)N[C@H](CNC(=O)[C@@H](C)NC(=O)[C@H](Cc1c(C)cc(O)cc1C)NC(=N)N)Cc1ccccc1] | Pd/C, H₂, MeOH, rt, 50 psi (~345 kPa) (0.085 mmol) Yield = 100% | 1Hnmr (400 MHz, MeOD4) □: 1.15 (d, 3H), 1.85 (s, 3H), 2.26 (s, 6H), 2.66 (dd, 1H), 2.81 (dd, 1H), 2.98 (dd, 1H), 3.12-3.23 (m, 4H), 4.12-4.28 (m, 2H), 6.50 (s, 2H), 7.16-7.28 (m, 5H). LRMS: ES⁺ m/z 497 [MH+] |
| 9 | Prep. 48 | 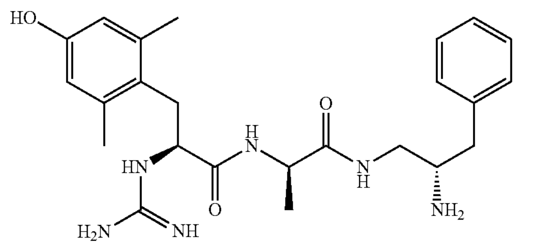 [SMILES: Cc1cc(O)cc(C)c1C[C@H](NC(=N)N)C(=O)N[C@H](C)C(=O)NC[C@@H](N)Cc1ccccc1] | MeOH, Pd/C, H₂, rt, 60 psi (~414 kPa) (0.5 mmol) quantitative | 1H NMR (400 MHz, CD3OD) δ: 1.19 (d, 3H), 2.28 (s, 6H), 2.65-3.06 (m, 6H), 3.14-3.24 (m, 2H), 3.42-3.62 (m, 3H), 4.13-4.25 (m, 2H), 4.30-4.44 (m, 2H), 4.57 (bs, 2H), 5.48 (s, 1H), 6.49 (s, 2H), 7.21-7.39 (m, 5H). LRMS 455.17 [MH]⁺ |

Example 10

N-alpha-[amino(imino)methyl]-N-[(1R)-1-{[(2S)-2-{[amino(imino)methyl]amino}-3-phenypropyl]carbamoyl}-3-(methylsulfinyl)propyl]-2,6-dimethyl-L-tyrosinamide bis-trifluoroacetate

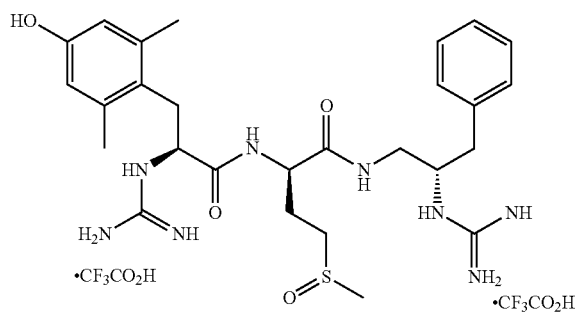 [SMILES: "·CF3CO2H" ; Cc1cc(O)cc(C)c1C[C@H](NC(=N)N)C(=O)N[C@H](CCS(C)=O)C(=O)NC[C@H](Cc1ccccc1)NC(=N)N ; "·CF3CO2H"]

To a solution of di-tert-butyl {(1Z,3S,7R,10S,12Z)-3-benzyl-12-[(tert-butoxycarbonyl)amino]-10-(4-hydroxy-2,6-dimethylbenzyl)-16,16-dimethyl-7-[2-(methylsulfinyl)ethyl]-6,9,14-trioxo-15-oxa-2,5,8,11,13-pentaazaheptadec-12-en-1-yl-1-ylidene}biscarbamate (180 mg, 0.19 mmol) from preparation 50 in dichloromethane (3 mL) was added TFA (1 mL) and the mixture was stirred at room temperature for 5 hours. The reaction mixture was then concentrated under reduced pressure and the residue was purified by column chromatography (silica, 9% methanol in dichloromethane as eluant increasing to DCM/MeOH/NH₃ 80/20/2 as eluant) to afford the title compound as a colourless oil in 50% yield, 96 mg. ¹H NMR (400 MHz, CD₃OD) δ : 1.87-2.17 (m, 2H), 2.28 (s, 6H), 2.30-2.46 (m, 2H), 2.61 (d, 3H), 2.64-2.74 (m, 1H), 2.92-3.03 (m, 2H), 3.19-3.28 (m, 2H), 3.32-3.37 (m, 1H), 3.77-3.88 (m, 1H), 4.20-4.37 (m, 2H), 6.48 (s, 1.4H), 6.50 (s, 0.6H), 7.06-7.33 (m, 5H).
LRMS APCI m/z 573 [MH]⁺

Example 11

(S)-2-Guanidino-3-(4-hydroxy-2,6-dimethyl-phenyl)-N-[(R)-1-(3-phenyl-propylcarbamoyl)-ethyl]-propionamide

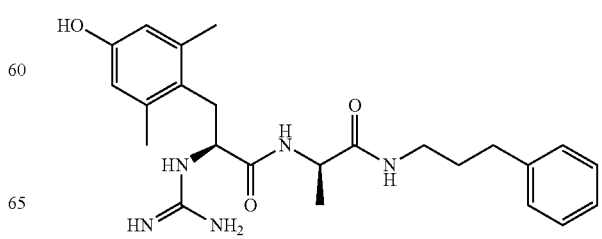

(S)-2-Amino-3-(4-hydroxy-2,6-dimethyl-phenyl)-N-[(R)-1-(3-phenyl-propylcarbamoyl)-ethyl]-propionamide (*J. Med. Chem.* 1994, 37, 888) (449 mg, 1.0 mmol) and 3,5-dimethylpyrazole-1-carboxamidine (240 mg, 1.2 mmol) were heated in ethanol at 60° C. After 24 hours, triethylamine (167 μl, 1.2 mmol) was added. The reaction was heated for a further 24 hours. The solvent was evaporated and the crude material was redissolved in dichloromethane containing 2% methanol. The resulting solution was washed with a solution of citric acid followed by sodium bicarbonate solution. The organic phase was washed with brine then dried over MgSO$_4$. The organics were filtered and evaporated leaving a small amount of a crude gum. The gum was purified using an ISCO chromatography system on a 12 g silica column using gradient elution from 95:5:0.5 to 80:20:5 DCM:MeOH:NH$_3$ to afford the title compound as a solid in 5% yield, 20 mg. $^1$H NMR (400 MHz, MeOH-d4) δ : 1.18 (d, 3H), 1.75-1.82 (m, 2H), 2.21 (s, 1H), 2.49 (s, 1H), 2.58-2.63 (m, 2H), 2.95-3.02 (m, 1H), 3.10-3.24 (m, 3H), 3.28-3.32 (m, 1H), 4.18-4.22 (m, 1H), 4.35-4.40 (m, 1H), 6.51 (s, 2H), 7.08-7.28 (m, 5H). LRMS m/z 440 [M+H]$^+$.

Example 12

N-carbamimidoyl-2,6-dimethyl-L-tyrosyl-N-[(2S)-2-carbamimidamido-3-phenylpropyl]-D-argininamide

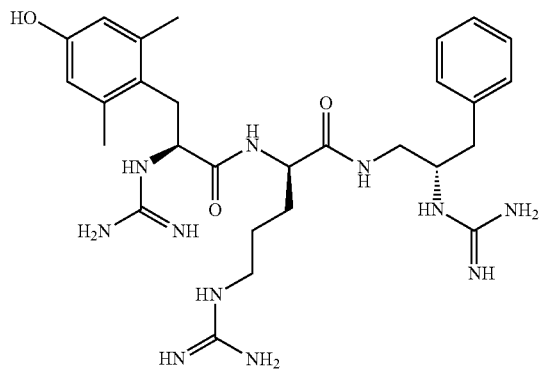 [SMILES: Cc1cc(O)cc(C)c1C[C@H](NC(=N)N)C(=O)N[C@H](CCCNC(=N)N)C(=O)NC[C@H](Cc1ccccc1)NC(=N)N]

The title compound was prepared from the product of Preparation 55 using the method of Example 10 on a scale of 400 mg in a yield of 64% following purification by reverse phase column chromatography (C-18, 26 g, 8 ml/minute, 5% to 15% CH$_3$CN in water).

$^1$H NMR (400 MHz, D$_2$O) δ: 0.91-1.17 (m, 2H), 1.25-1.37 (m, 1H), 1.40-1.51 (m, 1H), 2.12 (s, 6H), 2.54 (dd, 1H), 2.84-3.00 (m, 4H), 3.06 (dd, 1H), 3.23 (dd, 1H), 3.29 (dd, 1H), 3.69-3.75 (m, 1H), 3.92 (dd, 1H), 4.13 (dd, 1H), 6.49 (s, 2H), 7.14 (m, 2H), 7.17-7.28 (m, 3H)

LRMS ES+ m/z: 291 [M+2H]$^{2+}$

PREPARATIONS

Preparation 1

Benzyl [(1S)-1-benzyl-2-({(2R)-2-[(tert-butoxycarbonyl)amino]propanoyl}amino)ethyl]carbamate

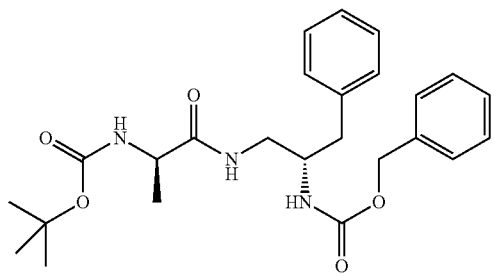 [SMILES: C[C@@H](NC(=O)OC(C)(C)C)C(=O)NC[C@H](Cc1ccccc1)NC(=O)OCc1ccccc1]

To a solution of N-(tert-butoxycarbonyl)-D-alanine (595 mg, 3.14 mmol) in DMF (20 mL) was added benzyl [(1S)-2-amino-1-benzylethyl]carbamate (Tet. Lett. 2005, 46(41), 7069) (968 mg, 3.30 mmol), HBTU (1.43 g, 3.77 mmol) and triethylamine (1.8 ml, 12.6 mmol) at room temperature. After stirring the reaction mixture for 15 hours, water (20 mL) was added to the mixture. The mixture was extracted with ethyl acetate/heptane 5/1 (2×20 mL) and the combined extracts were washed with 1N citric acid (20 mL), saturated aqueous sodium bicarbonate (20 mL) and brine (20 mL). The organic layer was dried over sodium sulfate, and concentrated under reduced pressure to afford the title compound as a white solid in 99% yield, 1.42 g. $^1$H NMR (400 MHz, CDCl$_3$) δ : 1.24 (d, 3H), 1.43 (s, 9H), 2.59-2.86 (m, 4H), 3.13-3.25 (m, 2H), 3.34-3.44 (m, 1H), 3.89-4.05 (m, 2H), 4.90-5.05 (m, 2H), 7.11-7.36 (m, 10H).

Preparations 2-17 were similarly prepared according to the method described above for preparation 1, starting from the appropriate respective amine and acid as mentioned below.

Preparation 2

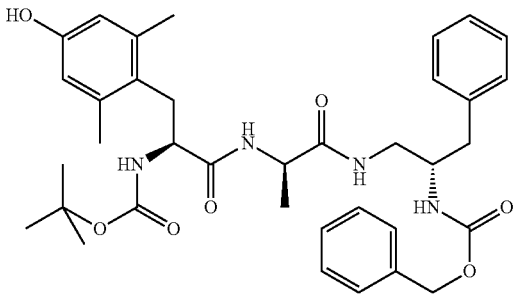 [SMILES: Cc1cc(O)cc(C)c1C[C@H](NC(=O)OC(C)(C)C)C(=O)N[C@H](C)C(=O)NC[C@H](Cc1ccccc1)NC(=O)OCc1ccccc1]

The above compound was made starting with the amine from Preparation 18 and the acid below:

(Bioorganic & Medicinal Chemistry Letters (2005), 15(3), 599-602).
Conditions: HOBt, EDC, NMM, DMF (2.59 mmol)
Yield=83%
$^1$H NMR (400 MHz, MeOH-d4) δ : 1.05 (d, 3H), 1.34 (s, 9H), 2.23 (s, 6H), 2.64-2.89 (m, 4H), 3.00-3.09 (m, 1H), 3.13-3.22 (m, 1H), 3.33-3.43 (m, 1H), 3.85-4.23 (m, 3H), 4.89-5.05 (m, 2H), 6.45 (s, 2H), 7.08-7.38 (m, 10H).
LRMS APCI m/z 647 [MH]$^+$ Preparation 3

Amine:

(J. Med. Chem. 2009, 52(3), 779)
Acid: Preparation 53
Conditions:
HOBt, EDC, NMM, DMF
(3.20 mmol)
Yield=95%
Product:
Mixture of Epimers Derived from Racemic Sulphoxide $^1$H NMR (400 MHz, MeOH-d4) δ : 1.31 (s, 9H), 2.60 (s, 3H), 2.62-2.99 (m, 6H), 3.14-3.23 (m, 1H), 3.32-3.36 (m, 1H), 3.76-3.92 (m, 1H), 4.88-4.96 (m, 1H), 7.11-7.28 (m, 5H), 7.80-7.93 (m, 4H).

Preparation 4

Amine: Preparation 49
Acid:

Conditions: HOBt, EDC, NMM, DMF (3.20 mmol)
Yield=100%
Product:
Mixture of Epimers Derived from Racemic Sulphoxide 1H NMR (400 MHz, CD3OD) δ : 1.33 (s, 9H), 1.35 (s, 9H), 1.64-2.16 (m, 2H), 2.25 (s, 6H), 2.29-2.44 (m, 1H), 2.56 (s, 3H), 2.58-2.84 (m, 4H), 3.02-3.15 (m, 2H), 3.37-4.30 (m, 4H), 6.45 (s, 1.4H), 6.46 (s, 0.6H), 7.12-7.29 (m, 5H)
LRMS ES m/z 689 [MH]$^+$ Preparation 5

Amine:

Tet. Asymm 1999, 10(18), 3571

Acid:

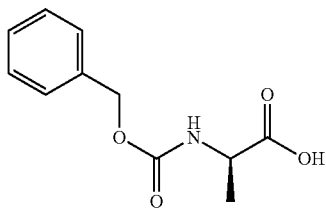 [SMILES: C[C@@H](NC(=O)OCc1ccccc1)C(=O)O]

Conditions: EDC, HOBt, NMM, DMF (1.28 mmol)
Yield=97%

Product:

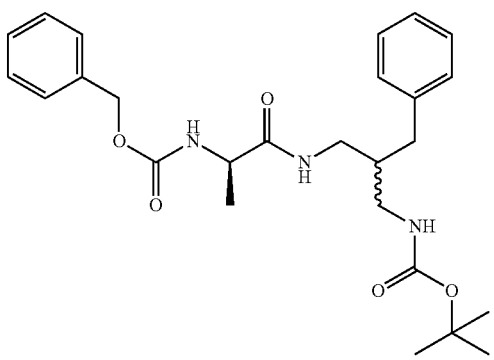 [SMILES: C[C@@H](NC(=O)OCc1ccccc1)C(=O)NCC(CNC(=O)OC(C)(C)C)Cc1ccccc1]

Mixture of Epimers
$^1$H NMR (400 MHz, MeOH-d4) δ : 1.33 (d, 3H), 1.43 (s, 9H), 1.91-1.98 (m, 1H), 2.53 (br d, 2H), 2.89-3.21 (m, 4H), 4.07-4.12 (m, 1H), 5.09 (s, 2H), 7.14-7.37 (m, 10H).

Preparation 6

Amine: Preparation 34
Acid:

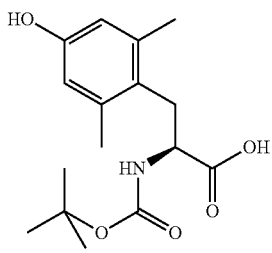

Conditions: EDC, HOBt, NMM, DMF (0.848 mmol)
Yield=87%

Product:

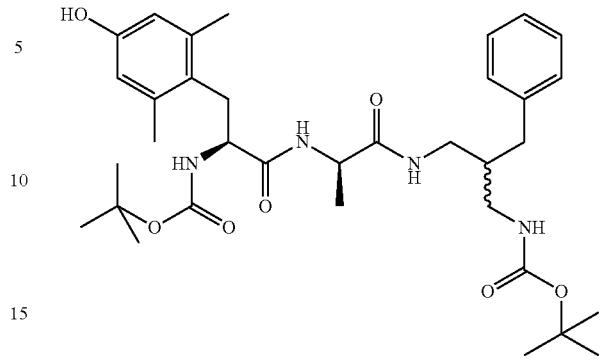

Mixture of Epimers
$^1$H NMR (400 MHz, MeOH-d4) δ : 1.10 (d, 3H), 1.36 (d, 9H), 1.42 (s, 9H), 2.0-2.01 (m, 1H), 2.24 (s, 6H), 2.55 (d, 2H), 2.83-3.14 (m, 6H), 4.01-4.07 (m, 1H), 4.18-4.22 (m, 1H), 6.46 (s, 2H), 7.13-7.26 (m, 5H).

Preparation 7

Amine: Preparation 22
Acid:

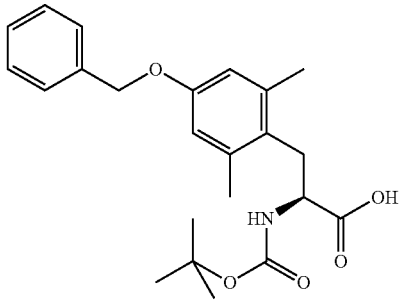 [SMILES: Cc1cc(OCc2ccccc2)cc(C)c1C[C@H](NC(=O)OC(C)(C)C)C(=O)O]

(Commercially available)
Conditions: EDC, HOBt, DIPEA, DMF (0.335 mmol)
Yield=98%
Product:

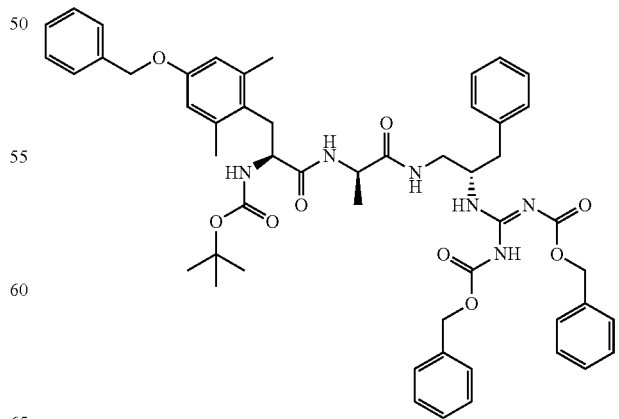

LRMS ES m/z 913 [MH]$^+$

Preparation 8

Amine:

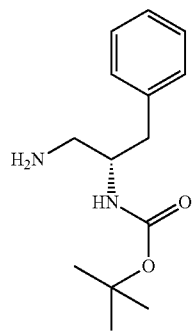 [SMILES: CC(C)(C)OC(=O)N[C@H](CN)Cc1ccccc1]

Tet. Asymm 1999, 10(18), 3571

Acid:

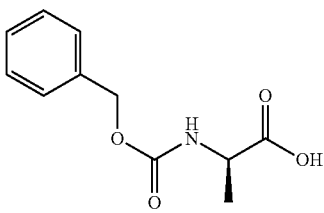 [SMILES: C[C@@H](NC(=O)OCc1ccccc1)C(=O)O]

Conditions: EDC, HOBt, DCM (7.39 mmol)
Yield=108% (contains DCM)
Product:

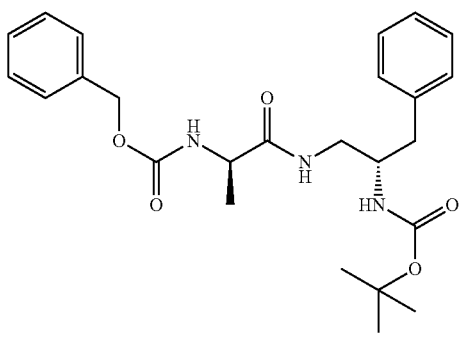 [SMILES: C[C@@H](NC(=O)OCc1ccccc1)C(=O)NC[C@H](Cc1ccccc1)NC(=O)OC(C)(C)C]

$^1$H NMR (400 MHz, CDC$_3$) δ : 1.37 (d, 3H), 1.38 (s, 9H), 2.69-2.80 (m, 1H), 2.82-2.85 (m, 1H), 3.30 (br s, 2H), 3.92 (br s, 1H), 4.18-4.22 (m, 1H), 4.85 (br s, 1H), 5.05-5.14 (m, 2H), 5.44 (br s, 1H), 6.73 (br s, 1H), 7.16-7.29 (m, 10H).

LRMS APCI m/z 456 [MH]$^+$

Preparation 9

Amine: Preparation 36

Acid:

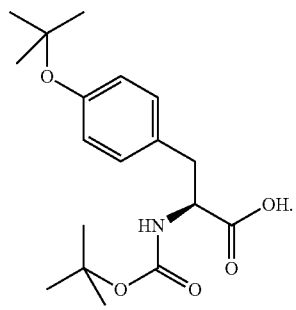 [SMILES: CC(C)(C)OC(=O)N[C@@H](Cc1ccc(OC(C)(C)C)cc1)C(=O)O]

(J. Med. Chem. 1992, 35(2), 223)

Conditions: EDC, HOBt, NMM, DMF (0.632 mmol)
Yield=88%

Product:

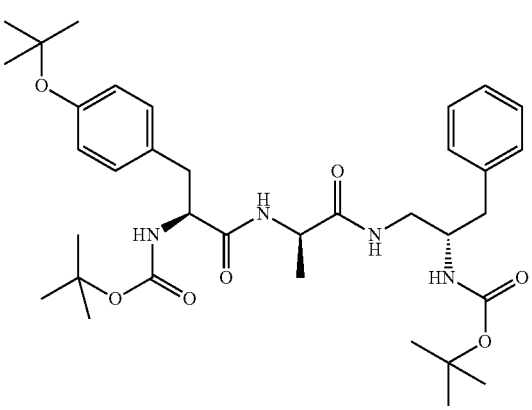 [SMILES: C[C@@H](NC(=O)[C@H](Cc1ccc(OC(C)(C)C)cc1)NC(=O)OC(C)(C)C)C(=O)NC[C@H](Cc1ccccc1)NC(=O)OC(C)(C)C]

$^1$H NMR (400 MHz,) δ : 1.17 (d, 3H), 1.31 (s, 9H), 1.33 (s, 9H), 1.35 (s, 9H), 2.65-2.98 (m, 4H), 3.12-3.33 (m, 2H), 3.80-3.87 (m, 1H), 4.14-4.24 (m, 2H), 6.90-6.92 (m, 2H), 7.11-7.26 (m, 7H).

Preparation 10

Amine: Preparation 25

Acid:

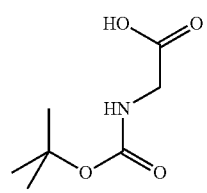

Conditions: EDC, HOBt, DIPEA, DCM (1.560 mmol)

Product:

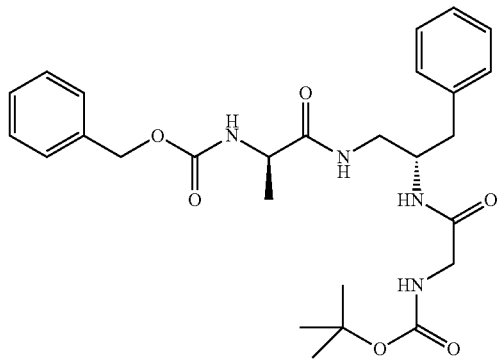 [SMILES: C[C@@H](NC(=O)OCc1ccccc1)C(=O)NC[C@H](Cc1ccccc1)NC(=O)CNC(=O)OC(C)(C)C]

¹H NMR (400 MHz, DMSO-d6) δ : 1.20 (d, 3H), 1.37 (s, 9H), 2.61 (dd, 1H), 2.73 (dd, 1H), 3.07-3.15 (m, 2H), 3.32 (s, 1H), 3.38-3.55 (m, 2H), 3.95-4.05 (m, 2H), 5.02 (s, 2H), 6.77 (br t, 1H), 7.15-7.38 (m, 10H), 7.64 (br d, 1H), 7.86 (br t, 1H).

LRMS APCI m/z 513 [MH]

Preparation 11

Amine: Preparation 37
Acid:

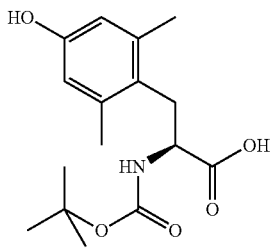

Conditions: EDC, HOBt, NMM, DMF (0.5280 mmol)
Yield=85%
Product:

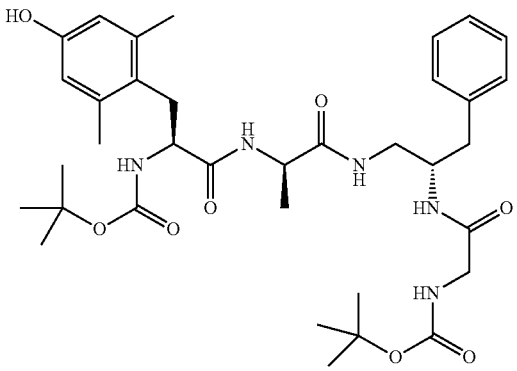 [SMILES: Cc1cc(O)cc(C)c1C[C@H](NC(=O)OC(C)(C)C)C(=O)N[C@H](C)C(=O)NC[C@H](Cc1ccccc1)NC(=O)CNC(=O)OC(C)(C)C]

LRMS ES m/z 670 [MH]+

Preparation 12

Amine: Preparation 25
Acid:

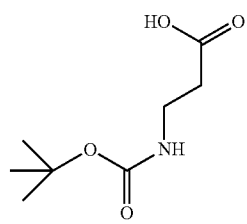

Conditions: EDC, HOBt, DIPEA, DCM (1.560 mmol)
Yield=95%
Product:

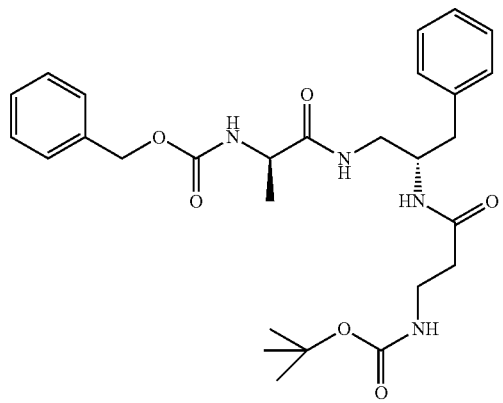 [SMILES: C[C@@H](NC(=O)OCc1ccccc1)C(=O)NC[C@H](Cc1ccccc1)NC(=O)CCNC(=O)OC(C)(C)C]

¹H NMR (400 MHz, DMSO-d6) δ : 0.99 (d, 3H), 1.23 (s, 9H), 2.12-2.17 (m, 2H), 2.58 (dd, 1H), 2.73 (dd, 1H), 3.03 (br q, 2H), 3.12 (br t, 2H), 3.97-4.05 (m, 2H), 4.96-5.06 (m, 2H), 6.63 (br t, 1H), 7.15-7.40 (m, 10H), 7.72 (br d, 1H), 7.89 (br t, 1H).

LRMS ES m/z 527 [MH]+

Preparation 13

Amine: Preparation 38
Acid:

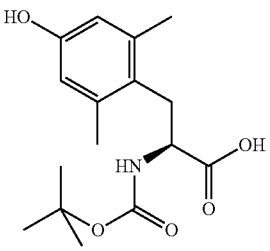 [SMILES: Cc1cc(O)cc(C)c1C[C@H](NC(=O)OC(C)(C)C)C(=O)O]

Conditions: EDC, HOBt, NMM, DMF (0.446 mmol)
Yield=51%

Product:

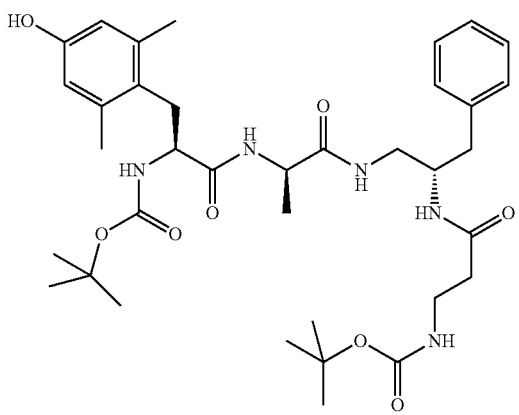 [SMILES: Cc1cc(O)cc(C)c1C[C@H](NC(=O)OC(C)(C)C)C(=O)N[C@H](C)C(=O)NC[C@H](Cc1ccccc1)NC(=O)CCNC(=O)OC(C)(C)C]

¹H NMR (400 MHz, MeOH-d4) δ : 1.00 (d, 3H), 1.29 (s, 9H), 1.32 (s, 9H), 2.12-2.18 (m, 1H), 2.15 (s, 6H), 2.58-2.64 (m, 1H), 2.74 (td, 2H), 2.95 (dd, 1H), 3.03-3.17 (m, 4H), 3.26-2.31 (m, 1H), 3.97-4.03 (m, 1H), 4.03-4.13 (m, 2H), 6.35 (s, 2H), 7.05-7.18 (m, 5H).
LRMS ES m/z 684 [MH]

Preparation 14

Amine: Preparation 29
Acid:

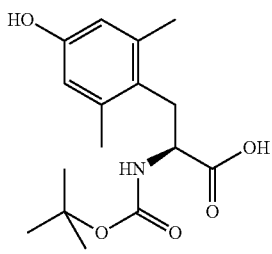

Conditions: NMM, IBCF, THF/DMF; −20 C (1.4 mmol); Yield=82%
Product:

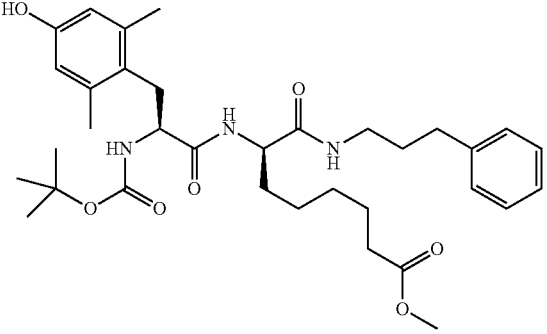 [SMILES: COC(=O)CCCCC[C@@H](NC(=O)[C@H](Cc1c(C)cc(O)cc1C)NC(=O)OC(C)(C)C)C(=O)NCCCc1ccccc1]

LRMS ES m/z 612 [MH]⁺
(Progressed directly to boc-deprotection)

Preparation 15

Amine:

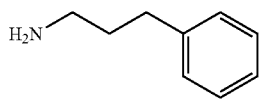

(commercial)

Acid:

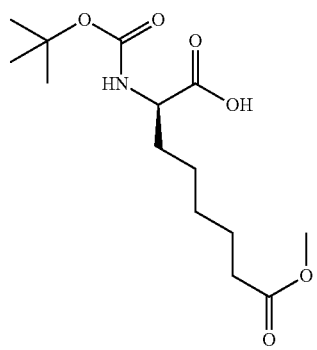 [SMILES: COC(=O)CCCCC[C@@H](NC(=O)OC(C)(C)C)C(=O)O]

(commercial)
Conditions: NMM, IBCF, THF/DMF; −40 C (1.7 mmol)
Yield=91%
Product:

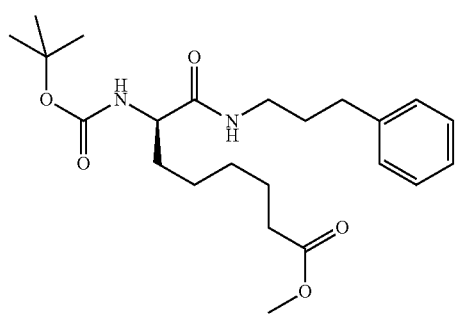 [SMILES: COC(=O)CCCCC[C@@H](NC(=O)OC(C)(C)C)C(=O)NCCCc1ccccc1]

LRMS ES m/z 422 [MH]⁺

Preparation 16

Amine:

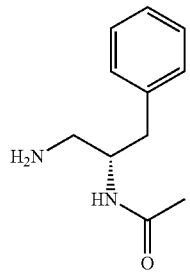

(See EP109023)
Acid: Boc-D-Ala-OH
Conditions: DIEA; EDC, HOAt, DMF; Yield=74%
Product:

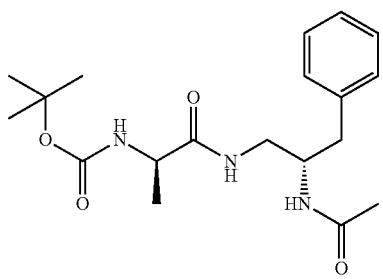 [SMILES: CC(=O)N[C@H](CNC(=O)[C@@H](C)NC(=O)OC(C)(C)C)Cc1ccccc1]

¹H NMR (400 mHz, DMSO-d6) δ 1.13(d, 3H), 1.34(s, 9H), 1.70(s, 3H), 2.53(m, 1H), 2.70(m, 1H), 2.99(m, 1H), 3.18(m, 1H), 3.90(m, 2H), 6.89(m, 1H), 7.18(m, 3H), 7.24(m 2H), 7.68(m. 1H), 7.94(m, 1H)
LRMS m/z (API+) 364 [M+H]

Preparation 17

Amine: Preparation 31
Acid:

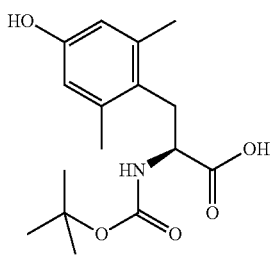

Conditions: DIEA, EDC, HOAt, DMF
Yield=59%
Product:

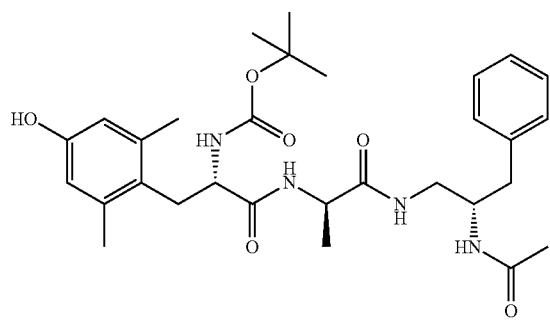 [SMILES: CC(=O)N[C@H](CNC(=O)[C@@H](C)NC(=O)[C@H](Cc1c(C)cc(O)cc1C)NC(=O)OC(C)(C)C)Cc1ccccc1]

¹H NMR (400 mHz, DMSO-d6) δ 1.02(d 3H), 1.30(s, 9H), 1.71(s, 3H), 2.16(s, 6H), 2.57(m, 1H), 2.71(m, 2H), 2.89(m, 1H), 3.06(m, 2H), 4.01(m, 2H), 4.17(m, 1H), 6.32(s, 2H), 6.91(d, 1H), 7.16(m, 3H), 7.24(m, 2H), 7.64(d, 1H), 7.74(d, 1H), 7.83(t, 1H), 8.90(s, 1H)
LRMS m/z (ESI+) 555 [M+H]

Preparation 18

Benzyl [(1S)-2-(D-alanylamino)-1-benzylethyl]carbamate

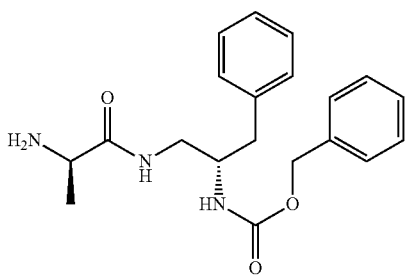 [SMILES: C[C@@H](N)C(=O)NC[C@H](Cc1ccccc1)NC(=O)OCc1ccccc1]

To a solution of benzyl [(1S)-1-benzyl-2-({(2R)-2-[(tert-butoxycarbonyl)amino]propanoyl}amino)ethyl]carbamate (1.43 g, 3.14 mmol) from preparation 1 in dichloromethane (30 mL) and methanol (2 mL) was added TFA (20 ml) at 0° C. The reaction mixture was stirred for 5 hours and then concentrated under reduced pressure. The residue was dissolved in methanol (5 mL) and loaded onto a 20 g SCX2 cartridge (pre-wetted with methanol). The cartridge was eluted with methanol to remove non-basic impurities and then eluted with 3M $NH_3$ in methanol. Fractions containing the title compound were combined and concentrated under reduced pressure to afford the title compound as a white solid in 90% yield, 1.01 g. ¹H NMR (400 MHz, MeOH-d4) δ : 1.21 (d, 3H), 2.70 (dd, 1H), 2.78-2.84 (m, 1H), 3.17 (dd, 1H), 3.31-3.44 (m, 3H), 3.88-4.01 (m, 2H), 4.98 (s, 2H), 7.11-7.34 (m, 10H).

Preparations 19-32 were similarly prepared according to the method described above for preparation 18, starting from the appropriate boc protected amine.

| Prep. | Precursor | Product | Conditions | Data |
|---|---|---|---|---|
| 19 | Prep 39 | HO—[structure] | TFA/DCM (0.523 mmol) Yield = 87% | ¹H NMR (400 MHz, MeOH-d4) δ : 1.03 (d, 3H), 2.23 (s, 6H), 2.72-2.98 (m, 6H), 3.38-3.51 (m, 2H), 3.73-3.79 (m, 1H), 4.10-4.20 (m, 2H), 4.43-4.64 (m, 2H), 5.06 (d, 2H), 5.19 (s, 2H), 5.48 (s, 2H), 6.46 (s, 2H), 7.07-7.44 (m, 15H); LRMS APCI m/z 723 [MH]⁺ |

-continued

| Prep. | Precursor | Product | Conditions | Data |
|---|---|---|---|---|
| 20 | Preparation 49 | 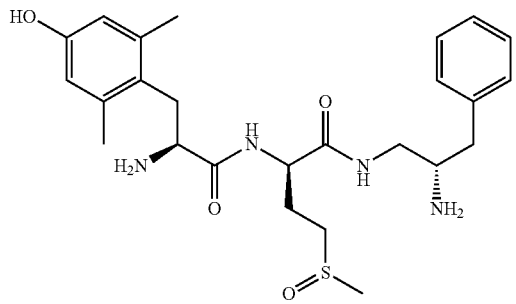 Mixture of epimers derived from racemic sulphoxide | TFA/DCM (0.726 mmol) Yield = 98% | ¹H NMR (400 MHz, CD3OD) δ: 1.76-2.24 (m, 3H), 2.26 (s, 6H), 2.27-2.43 (m, 1H), 2.56 (s, 3H), 2.57-3.25 (m, 7H), 3.44-3.56 (m, 1H), 4.13-4.34 (m, 1H), 6.44 (s, 1.3H), 6.46 (s, 0.7H), 7.16-7.35 (m, 5H) LRMS ES m/z 489 [MH]⁺ |
| 21 | Preparation 6 | 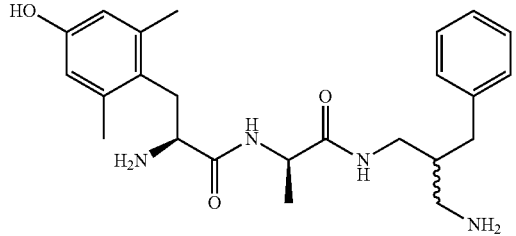 Mixture of epimers | TFA, DCM (0.796 mmol) Yield = 100% | ¹H NMR (400 MHz, MeOH-d4) δ: 1.11 (dd, 3H), 1.88-1.94 (m, 1H), 2.25 (s, 6H), 2.46-2.60 (m, 4H), 2.81 (dd, 1H), 2.92-2.99 (m, 1H), 3.18-3.25 (m, 2H), 3.45 (dd, 1H), 4.19 (q, 1H), 6.46 (s, 2H), 7.16-7.28 (m, 5H). |
| 22 | Preparation 42 | 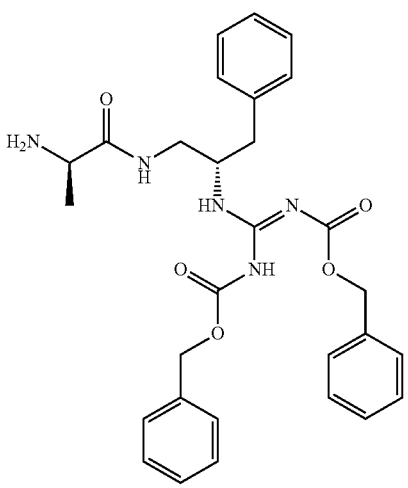 [SMILES: C[C@@H](N)C(=O)NC[C@H](Cc1ccccc1)N/C(=N/C(=O)OCc1ccccc1)NC(=O)OCc1ccccc1] | TFA, DCM (0.396 mmol) Yield = 84% | ¹H NMR (400 MHz, CD₃Cl) δ: 1.21 (d, 3H), 2.72-2.84 (m, 2H), 3.16-3.23 (m, 1H), 3.38-3.43 (m, 1H), 3.56 (br d, 1H), 4.38-4.43 (m, 1H), 5.00 (q, 2H), 5.04-5.09 (m, 2H), 7.11-7.29 (m, 15H), 7.98 (br s, 1H), 8.35 (d, 1H), 11.49 (br s, 1H). LRMS ES m/z 532 [MH]⁺ |

| Prep. | Precursor | Product | Conditions | Data |
|---|---|---|---|---|
| 23 | Preparation 7 | (structure) | 4M HCl in dioxane (0.4160 mmol) Yield = 92% | $^1$H NMR (400 MHz, CD$_3$Cl) δ : 1.23 (d, 3H), 2.32 (s, 6H), 2.77 (dd, 1H), 2.88 (dq, 2H), 3.16 (dd, 1H), 3.28 (ddd, 1H), 3.35-3.65 (m, 2H), 4.33 (quin, 1H), 4.46-4.50 (m, 1H), 5.01 (s, 2H), 5.08-5.18 (m, 4H), 6.67 (s, 2H), 7.14-7.51 (m, 20H), 8.46 (d, 1H), 11.62 (br s, 1H). LRMS ES m/z 813 [MH]$^+$ |
| 24 | Preparation 9 | (structure) | TFA, DCM (0.555 mmol) Yield = 89% | $^1$H NMR (400 MHz, MeOH-d4) δ : 1.18 (d, 3H), 2.53-2.58 (m, 1H), 2.72-2.86 (3H), 3.07-3.20 (m, 3H), 3.47 (t, 1H), 4.20 (q, 1H), 6.30 (d, 2H), 7.01 (d, 2H), 7.20-7.31 (m, 5H). |
| 25 | Preparation 8 | (structure) | 4M HCl in dioxane (3.12 mmol) Yield = 100% | LRMS ES m/z 356 [MH]$^+$ |
| 26 | Preparation 11 | (structure) | TFA, DCM (0.448 mmol) Yield = 93% | LRMS ES m/z 470 [MH]$^+$ |

| Prep. | Precursor | Product | Conditions | Data |
|---|---|---|---|---|
| 27 | Preparation 13 | (structure) | TFA, DCM (0.234 mmol) Yield = 49% | LRMS ES m/z 484 [MH]+ |
| 28 | Preparation 52 | (structure) | 7M HCl in dioxane (3.12 mmol) Yield = 100% | LRMS ES m/z 498 [MH]+ |
| 29 | Preparation 15 | (structure) | 7M HCl in dioxane (2.59 mmol) Yield = 100% | LRMS ES m/z 321 [MH]+ |
| 30 | Preparation 17 | (structure) | 4.0M HCl in dioxane Yield = 83% (HCl salt) | $^1$H NMR (400 mHz, DMSO-d6) δ 0.88 (d, 3H), 1.73 (s, 3H), 2.17 (s, 6H), 2.57 (m, 1H), 2.71 (m, 1H), 2.94 (m, 3H), 3.19 (m, 1H), 3.77 (broad s, 4H), 3.94 (m, 1H), 4.13 (m, 1H), 7.23 (m, 5H), 7.86 (m, 2H), 8.11 (d, 1H), 8.46 (broad s, 3H), 9.08 (m, 1H) LRMS m/z (ESI+) 455 [M + H] |

| Prep. | Precursor | Product | Conditions | Data |
|---|---|---|---|---|
| 31 | Preparation 16 | | 4.0M HCl in dioxane Yield = 97% (HCl salt) | $^1$H NMR (400 mHz, DMSO-d6) δ 1.34 (d, 3H), 1.73 (s, 3H), 2.66 (m, 1H), 2.76 (m, 1H), 3.01 (m, 1H), 3.30 (m, 1H), 3.83 (m, 1H), 4.03 (m, 1H), 7.19 (m, 5H), 7.90 (d, 1H), 8.22 (s, 3H) LRMS m/z (ESI+) 264 [M + H] |
| 32 | Preparation 2 | | TFA, DCM (0.758 mmol) Yield = 96% | $^1$H NMR (400 mHz, CD3OD) δ: 1.03 (d, 3H), 2.24 (s, 6H), 2.62-2.99 (m, 5H), 3.07-3.24 (m, 2H), 3.39-3.50 (m, 2H), 3.80-3.99 (m, 2H), 4.10-4.36 (m, 2H), 4.90-5.03 (m, 2H), 5.48 (s, 1H), 6.46 (s, 2H), 7.07-7.33 (m, 10H). LRMS 547.18 [MH]$^+$ |

Preparation 33

N-(tert-butoxycarbonyl)-2,6-dimethyl-L-tyrosyl-N-[(2S)-2-amino-3-phenylpropyl]-D-alaninamide To a solution of N-(tert-butoxycarbonyl)-2,6-dimethyl-L-tyrosyl-N-[(2S)-2-{[(benzyloxy)carbonyl]amino}-3-phenylpropyl]-D-alaninamide (450 mg, 0.70 mmol) from preparation 2 in methanol (10 mL) was added palladium hydroxide (40 mg) and ammonium formate (231 mg, 3.48 mmol) at room temperature. The reaction was then heated at 60° C. for 3 hours, after this time the reaction was allowed to cool and then filtered through a pad of Arbocel. The filtrate was concentrated under reduced pressure, the residue dissolved in methanol (5 mL) and loaded onto a 20 g SCX2 cartridge (pre-wetted with methanol). The cartridge was eluted with methanol to remove non-basic impurities and then eluted with 3M NH$_3$ in methanol. Fractions containing the title compound were combined and concentrated under reduced pressure to afford the title compound as a white amorphous solid in 95% yield, 338 mg. $^1$H NMR (400 MHz, MeOH-d4) δ : 1.09 (d, 3H), 1.36 (s, 9H), 2.23 (s, 6H), 2.51-2.61 (m, 1H), 2.72-2.89 (m, 2H), 3.01-3.28 (m, 4H), 3.96-4.06 (m, 1H), 4.14-4.28 (m, 2H), 6.46 (s, 2H), 7.11-7.35 (m, 5H).

Preparations 34-38 were similarly prepared according to the method described above for preparation 33, starting from the appropriate cbz protected amine.

| Prep. | Precursor | Product | Conditions | Data |
|---|---|---|---|---|
| 34 | Preparation 5 | 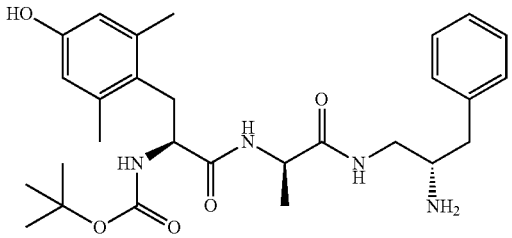 [SMILES: Cc1cc(O)cc(C)c1C[C@H](NC(=O)OC(C)(C)C)C(=O)N[C@H](C)C(=O)NC[C@@H](N)Cc1ccccc1] | Pd(OH)$_2$, H$_2$, MeOH, RT, 60 psi (~414 kPa) (1.25 mmol) Yield = 74% | $^1$H NMR (400 MHz, MeOH-d4) δ : 1.26 (dd, 3H), 1.43 (s, 9H), 1.98-2.05 (m, 1H), 2.57 (dd, 2H), 2.97-3.07 (m, 2H), 3.12-3.21 (m, 2H), 3.40 (q, 1H), 7.15-7.28 (m, 5H). |

| Prep. | Precursor | Product | Conditions | Data |
|---|---|---|---|---|
| 35 | Preparation 1 | 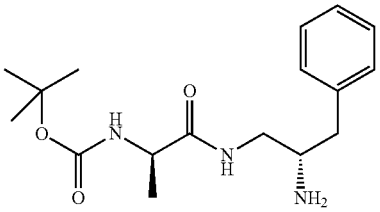 [SMILES: C[C@@H](NC(=O)OC(C)(C)C)C(=O)NC[C@@H](N)Cc1ccccc1] | Pd(OH)$_2$, H$_2$, EtOAc, RT, 60 psi (~414 kPa) (0.777 mmol) Yield = 80% | $^1$H NMR (400 MHz, CDCl$_3$)δ : 1.37 (d, 3H), 1.45 (s, 9H), 2.52 (dd, 1H), 2.81 (dd, 1H), 3.07-3.19 (m, 2H), 3.41-3.46 (m, 1H), 4.09-4.17 (m, 1H), 7.18-7.33 (m, 5H). |
| 36 | Preparation 8 | 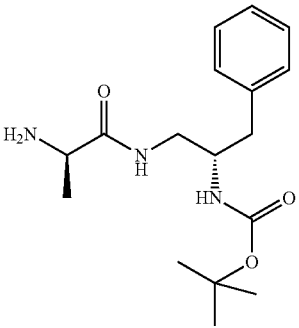 | 10% Pd/C, H$_2$, THF, RT (7.90 mmol) Yield = 92% | $^1$H NMR (400 MHz, CDCl$_3$)δ : 1.31 (d, 3H), 1.40 (s, 9H), 2.71 (dd, 1H), 2.91 (dd, 1H), 3.23-3.29 (m, 2H), 3.49 (q, 1H), 3.92-3.96 (m, 1H), 4.98 (br d, 1H), 7.16-7.22 (m, 3H), 7.24-7.32 (m, 2H), 7.56 (br s, 1H). LRMS APCI m/z 322 [MH]$^+$ |
| 37 | Preparation 10 | 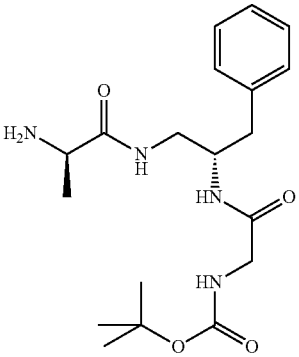 [SMILES: C[C@@H](N)C(=O)NC[C@H](Cc1ccccc1)NC(=O)CNC(=O)OC(C)(C)C] | 20% Pd(OH)$_2$, MeOH, RT, 60 psi (~414 kPa) 0.5740 mmol Yield = 93% | $^1$H NMR (400 MHz, DMSO-d6)δ : 1.24 (d, 3H), 1.44 (s, 9H), 2.72-2.85 (m, 3H), 3.35-3.43 (m, 2H), 3.48-3.65 (m, 2H), 4.21-4.28 (m, 1H), 7.16-7.28 (m, 5H). LRMS ES m/z 379 [MH]$^+$ |
| 38 | Preparation 12 | 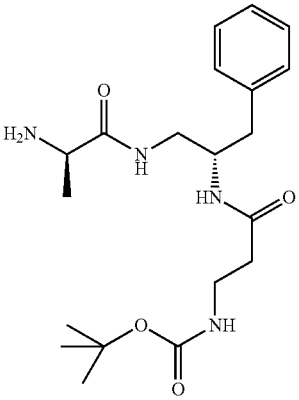 [SMILES: C[C@@H](N)C(=O)NC[C@H](Cc1ccccc1)NC(=O)CCNC(=O)OC(C)(C)C] | 20% Pd(OH)$_2$, MeOH, RT, 60 psi (~414 kPa) (0.57 mmol) Yield = 99% | $^1$H NMR (400 MHz, CDCl$_3$)δ : 1.35 (d, 3H), 1.43 (s, 9H), 2.34 (br t, 2H), 2.73 (dd, 1H), 2.93 (dd, 1H0, 3.31-3.37 (m, 4H), 3.54-3.61 (br m, 1H), 4.25-4.30 (m, 1H), 5.34 (br s, 1H), 6.58 (br s, 1H), 7.21-7.32 (m, 5H), 7.72 (br s, 1H). LRMS APCI m/z 393 [MH]$^+$ |

Preparation 39

N-(tert-butoxycarbonyl)-2,6-dimethyl-L-tyrosyl-N-[(2S)-2-{[(E)-{[(benzyloxy) carbonyl]amino}{[(benzyloxy)carbonyl]imino}methyl]amino}-3-phenylpropyl]-D-alaninamide

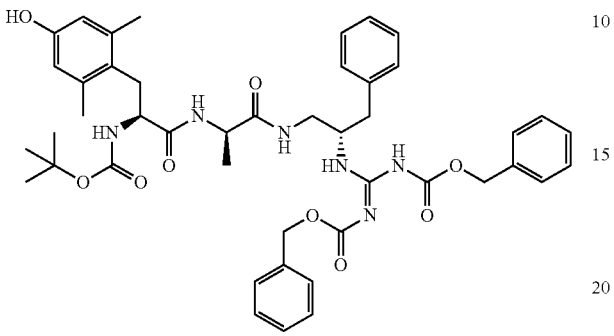

To a solution N-(tert-butoxycarbonyl)-2,6-dimethyl-L-tyrosyl-N-[(2S)-2-amino-3-phenylpropyl]-D-alaninamide (330 mg, 0.64 mmol) from preparation 33 in THF (5 mL) was added N,N'-Bis(benzyloxycarbonyl)-1H-pyrazole-1-carboxamidine (268 mg, 0.71 mmol) and N,N-diisopropylethylamine (173 uL, 0.97 mmol). The reaction was stirred for 2 hours at 60° C. and then quenched by the addition of water (5 mL). The mixture was extracted with ethyl acetate (10 mL), the extract was dried over sodium sulphate and concentrated under reduced pressure. The residue was purified by column chromatography (silica, 25% ethyl acetate in heptane as eluent increasing to 33%) to afford the title compound as a colourless oil in 81% yield, 430 mg. $^1$H NMR (400 MHz, MeOH-d4) δ : 1.05 (d, 3H), 1.28 (s, 9H), 2.22 (s, 6H), 2.73-3.11 (m, 4H), 3.41-3.52 (m, 1H), 3.95-4.23 (m, 2H), 4.38-4.59 (m, 2H), 4.98-5.28 (m, 4H), 6.45 (s, 2H), 7.09-7.46 (m, 15H). LRMS APCI m/z 823 [MH]$^+$ Preparations 40-48 were similarly prepared according to the method described above for preparation 39, starting from the appropriate amine.

Preparation 40

Precursor—Preparation 19
Product:

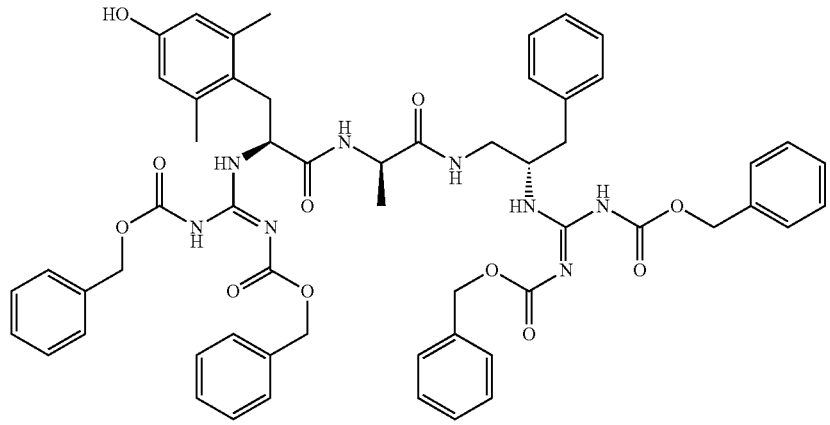 [SMILES: Cc1cc(O)cc(C)c1C[C@H](N/C(=N/C(=O)OCc1ccccc1)NC(=O)OCc1ccccc1)C(=O)N[C@H](C)C(=O)NC[C@H](Cc1ccccc1)N/C(=N\C(=O)OCc1ccccc1)NC(=O)OCc1ccccc1]

$^1$H NMR (400 MHz, MeOH-d4): δ : 1.06 (d, 3H), 2.28 (s, 6H), 2.57-2.71 (m, 2H), 2.75-2.88 (m, 2H), 2.93-3.13 (m, 4H), 3.37-3.50 (m, 1H), 4.26-4.70 (m, 8H), 4.95-5.19 (m, 6H), 5.48 (s, 1H), 6.45 (s, 2H), 7.03-7.43 (m, 25H); LRMS APCI m/z 1034 [MH]$^+$

Preparation 41

Precursor—Preparation 21

Product:

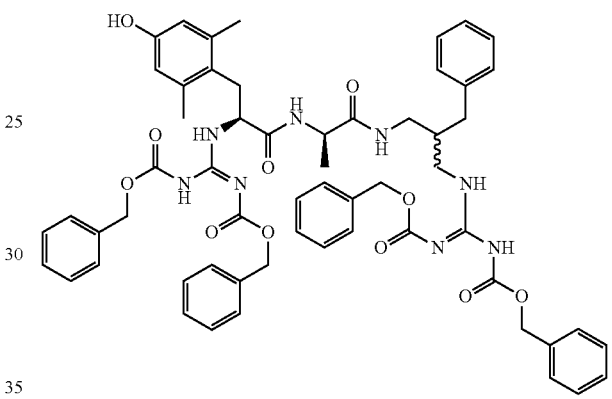

$^1$H NMR (400 MHz, MeOH-d4) δ : 0.72 (d, 1.5H), 0.78 (d, 1.5H), 1.93-2.06 (m, 1H), 2.29 (d, 6H), 2.34-2.40 (m, 1H), 2.52-2.62 (m, 1.5H), 2.72 (dd, 0.5H), 2.90 (dd, 0.5H), 2.95-3.19 (m, 3.5H), 3.25-3.40 (m, 1H), 3.47 (dd, 0.5H), 3.62-3.66 (m, 0.5H), 3.91 (q, 0.5H), 4.05 (q, 0.5H), 4.74-4.96 (m, 2H), 5.02-5.5.13 (m, 4H), 5.18 (d, 2H), 6.49 (d, 2H), 7.09-7.41 (m, 25H).

Preparation 42
Precursor—Preparation 35
Product:
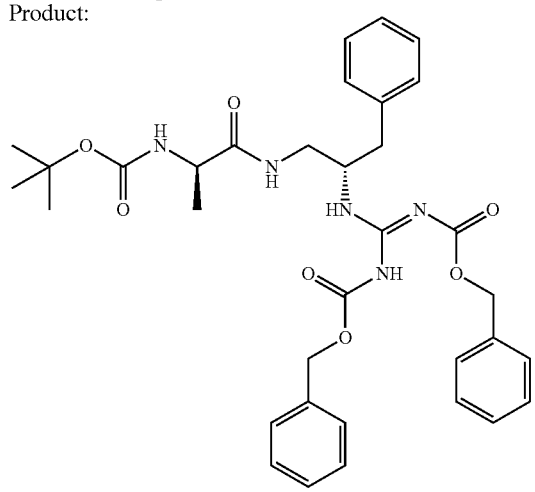
¹H NMR (400 MHz, CD₃Cl) δ : 1.20 (d, 3H), 1.43 (s, 9H), 2.83-2.92 (m, 2H), 3.34-3.39 (m, 1H), 3.48-3.53 (m, 1H), 4.04 (br s, 1H), 4.46 (br s, 1H), 5.12 (q, 2H), 5.18 (s, 2H), 7.20-7.42 (m, 15H), 8.49 (d, 1H), 11.60 (s, 1H).
LRMS ES m/z 632 [MH]⁺
Preparation 43
Precursor—Preparation 24
Product:
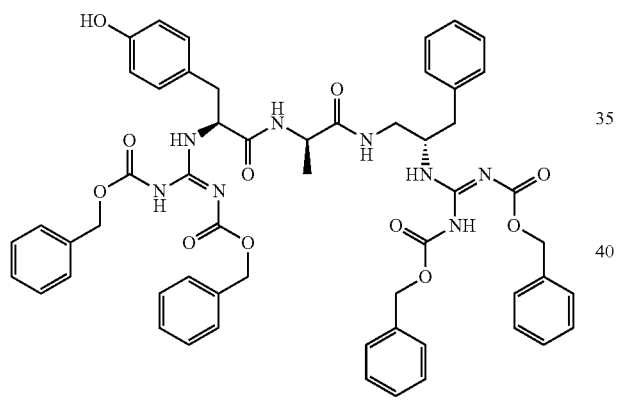
¹H NMR (400 MHz, MeOH-d4) δ : 1.14 (d, 3H), 2.63-2.68 (m, 1H), 2.81 (dd, 1H), 2.97 (d, 2H), 3.03 (dd, 1H), 3.42 (dd, 1H), 4.12 (q, 1H), 4.32-4.38 (m, 1H), 4.62 (t, 1H), 4.98-5.06 (m, 4H), 5.12 (s, 2H), 5.16 (d, 2H), 6.70 (d, 2H), 7.03 (d, 2H), 7.16-7.36 (m, 25H).
LRMS 857.46 [MH]⁺
Preparation 44
Precursor—Preparation 26
Product:
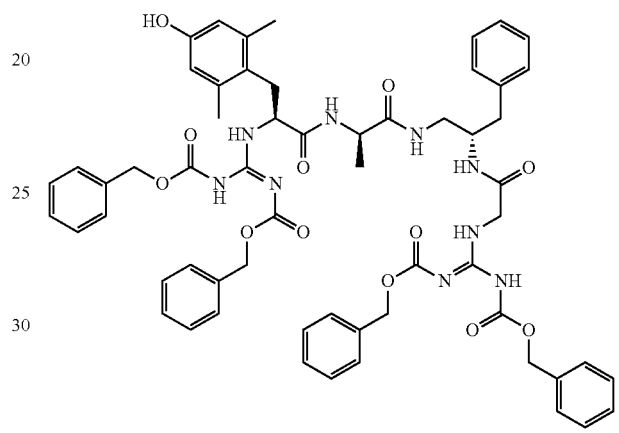
LRMS ES m/z 1091 [MH]⁺
Preparation 45
Precursor—Preparation 27
Product:
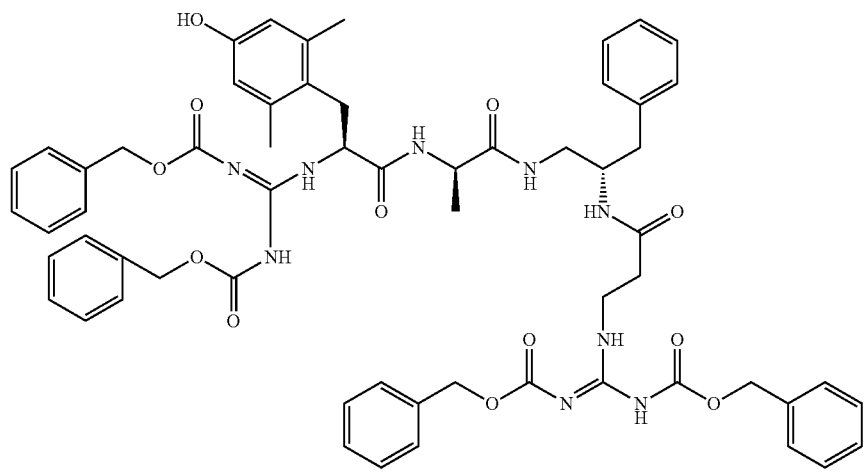 [SMILES: Cc1cc(O)cc(C)c1C[C@H](NC(=NC(=O)OCc1ccccc1)NC(=O)OCc1ccccc1)C(=O)N[C@H](C)C(=O)NC[C@H](Cc1ccccc1)NC(=O)CCN/C(=N\C(=O)OCc1ccccc1)NC(=O)OCc1ccccc1]
LRMS ES m/z 1091 [MH]⁺

Preparation 46

Precursor—Preparation 28
Product:

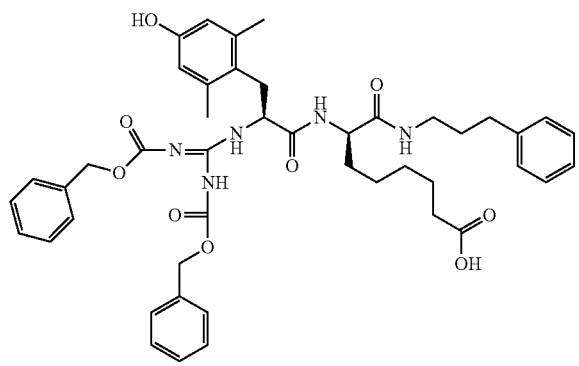 [SMILES: Cc1cc(O)cc(C)c1C[C@H](NC(=NC(=O)OCc1ccccc1)NC(=O)OCc1ccccc1)C(=O)N[C@H](CCCCCC(=O)O)C(=O)NCCCc1ccccc1]

LC-MS: Rt=3.38 min (100%)
LRMS: m/z 808 [MH+]

Preparation 47

Precursor—Preparation 30
Product:

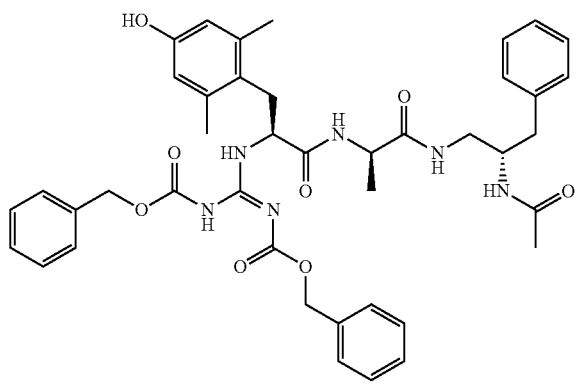 [SMILES: CC(=O)N[C@H](CNC(=O)[C@@H](C)NC(=O)[C@H](Cc1c(C)cc(O)cc1C)N/C(=N/C(=O)OCc1ccccc1)NC(=O)OCc1ccccc1)Cc1ccccc1]

¹H NMR (400 MHz, CDCl3) δ : 1.00 (d, 3H, Me), 1.81 (s, 3H, Ac), 2.30 (s, 6H, diMe), 2.58 (dd, 1H), 2.66 (dd, 1H), 3.02-3.17 (m, 2H), 3.22-3.33(m, 1H), 4.15 (m, 1H), 4.23 (m, 1H), 4.58 (m, 1H), 4.90 (d, 1H), 4.98 (d, 1H), 5.17 (q, 2H), 5.65 (d, 1H, NH), 5.85 (br, s, 1H, NH), 5.99 (s, 1H, NH), 6.50 (s, 2H, arom), 6.72 (t, 1H, NH), 7.08 (d, 1H, arom), 7.13-7.40 (m, 13H, arom), 8.90 (d, 1H, NH), 11.52 (s, 1H, OH)

LCMS ES m/z 765 [MH]⁺

Preparation 48

Precursor—Preparation 32
Product:

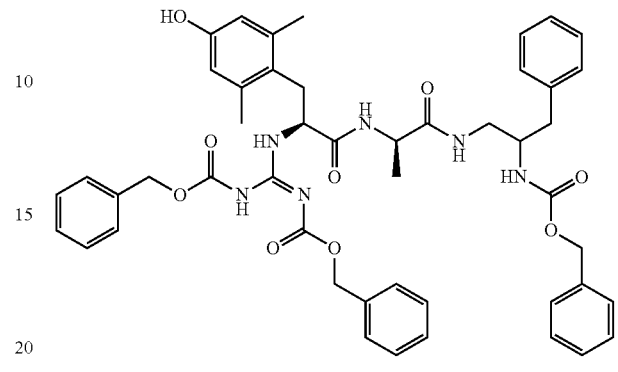

1H NMR (400 MHz, CD3OD) δ : 1.08 (d, 3H), 2.29 (s, 6H), 2.48-2.59 (m, 1H), 2.70-2.80 (m, 1H), 2.94-3.13 (m, 2H), 3.68-3.74 (m, 1H), 4.06-4.17 (m, 1H), 4.61-4.72 (m, 1H), 4.89-5.24 (m, 8H), 6.46 (s, 2H), 7.05-7.41 (m, 15H).

Preparation 49 tert-butyl [(1S)-2-F[(2R)-2-amino-4-(methylsulfinyl)butanoyl]amino}-benzylethyl]carbamate

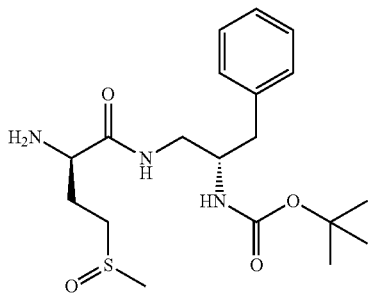 [SMILES: CS(=O)CC[C@@H](N)C(=O)NC[C@H](Cc1ccccc1)NC(=O)OC(C)(C)C]

A mixture of tert-butyl [(1S)-1-benzyl-2-{[(2R)-2-(1,3-dioxo-1,3-dihydro-2H-isoindol-2-yl)-4-(methylsulfinyl)butanoyl]amino}ethyl]carbamate from preparation 3 (1.6 g, 3.03 mmol) and hydrazine monohydrate (0.44 mL, 9.10 mmol) in methanol (15 mL) was stirred at room temperature for 15 hours and then heated at reflux for 2 hours. The reaction mixture was then allowed to cool and the white precipitate was filtered off. The filtrate was concentrated under reduced pressure and the residue was triturated with dichloromethane and filtered. The filtrate was concentrated under reduced pressure to give the title compound as a mixture of epimers derived from the racemic sulphoxide, as a white amorphous solid in 100% yield, 1.27 g. ¹H NMR (400 MHz, MeOH-d4) δ : 1.35 (s, 9H), 1.84-2.18 (m, 2H), 2.63 (s, 3H), 2.66-2.98 (m, 4H), 3.08-3.23 (m, 1H), 3.36-3.49 (m, 2H), 3.80-3.95 (m, 1H), 7.13-7.32 (m, 5H). LRMS ES m/z 398 [MH]⁺

Preparation 50 di-tert-butyl{(1Z,3S,7R,10S,12Z)-3-benzyl-12-[(tert-butoxycarbonyl)amino]-10-(4-hydroxy-2,6-dimethylbenzyl)-16,16-dimethyl-7-[2-(methylsulfinyl)ethyl]-6,9,14-trioxo-15-oxa-2,5,8,11,13-pentaazaheptadec-12-en-1-yl-1-ylidene}biscarbamate

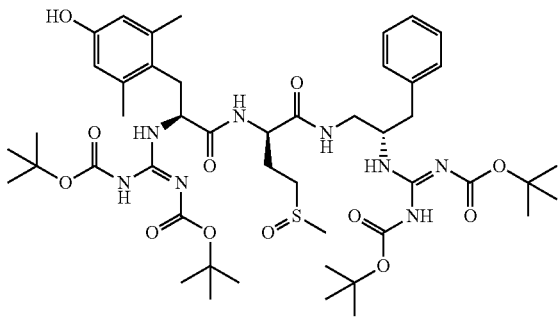 [SMILES: Cc1cc(O)cc(C)c1C[C@H](N/C(=N/C(=O)OC(C)(C)C)NC(=O)OC(C)(C)C)C(=O)N[C@H](CCS(C)=O)C(=O)NC[C@H](Cc1ccccc1)N/C(=N/C(=O)OC(C)(C)C)NC(=O)OC(C)(C)C]

To a solution of N-[(1R)-1-{[(2S)-2-amino-3-phenylpropyl]carbamoyl}-3-(methylsulfinyl)propyl]-2,6-dimethyl-L-tyrosinamide (195 mg, 0.399 mmol) from preparation 20 in dichloromethane (3 mL) was added di-tert-butyl [(E)-1H-pyrazol-1-ylmethylylidene]biscarbamate (272 mg, 0.878 mmol) and N,N-diisopropylethylamine (215 uL, 1.20 mmol). The reaction was then heated at reflux for 5 hours after which it was allowed to cool and then washed with 1N citric acid (3 mL), dried over magnesium sulphate and concentrated under reduced pressure. The residue was purified by column chromatography (silica, 50% ethyl acetate in heptane as eluant followed by DCM/MeOH/NH$_3$ 90/10/1 as eluant to afford the title compound as a yellow oil in 46% yield, 181 mg. (Mixture of epimers derived from racemic sulphoxide) 1H NMR (400 MHz, CD3OD) δ : 1.44 (s, 18H), 1.45 (s, 9H), 1.50 (s, 9H), 1.79-2.28 (m, 3H), 2.32 (s, 6H), 2.59 (s, 3H), 2.63-2.88 (m, 3H), 3.01-3.18 (m, 3H), 3.60-3.72 (m, 1H), 4.13-4.37 (m, 2H), 4.70-4.79 (m, 1H), 6.45 (s, 1.4H), 6.46 (s, 0.6H), 7.13-7.28 (m, 5H): LRMS APCI m/z 973 [MH]$^+$

Preparation 51

O-benzyl-N-[bis(dimethylamino)methylene]-2,6-dimethyl-L-tyrosyl-N-[(2S)-2-{[(Z)-{[(benzyloxy)carbonyl]amino}{[(benzyloxy)carbonyl]imino}methyl]amino}-3-phenylpropyl]-D-alaninamide formate salt

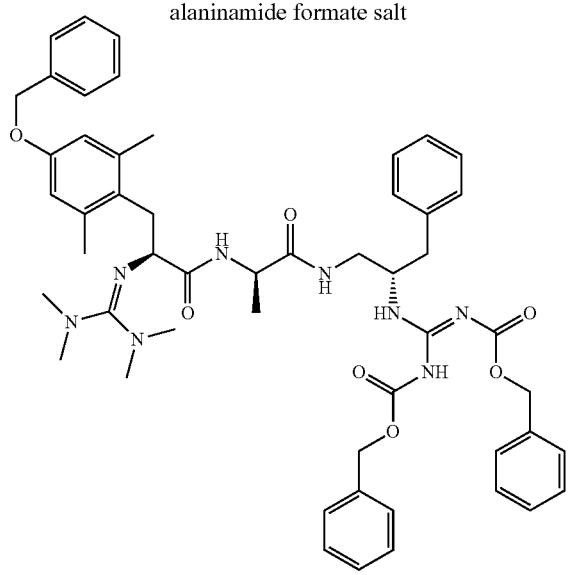

1,1,3,3-tetramethylurea (450 mg) was dissolved in anhydrous ether (5 mL) under N$_2$. Oxayl chloride (390 uL) was added over 1 minute and the mixture was left to stir. After 5 minutes a solid had precipitated on the base of the flask, this was broken up and stirring was continued overnight. Volatiles were evaporated to give N-[chloro(dimethylamino)methylene]-N-methylmethanaminium chloride salt as a white solid. Acetonitrile (10 mL) was added and 1 mL of this solution was added to a stirred solution of O-benzyl-2,6-dimethyl-L-tyrosyl-N-[(2S)-2-{[(Z)-{[(benzyloxy)carbonyl]amino}{[(benzyloxy)carbonyl]imino}methyl]amino}-3-phenylpropyl]-D-alaninamide (315 mg, 0.387 mmol) from preparation 23, and triethylamine (65 uL, 0.464 mmol) in acetonitrile (2 mL) under N$_2$ with ice cooling. The reaction mixture was then allowed to stir at room temperature overnight. LCMS showed starting material still remained so more of the N-[chloro(dimethylamino)methylene]-N-methylmethanaminium chloride salt solution (0.1 mL) was added and the reaction was left to stir over a weekend. The reaction mixture was then purified by Trilution HPLC (eluting with acetonitrile/H2O/formic acid gradient) to afford the title compound as a white foam in 24% yield, 90 mg. $^1$H NMR (400 MHz, MeOH-d4) δ : 0.92 (d, 3H), 2.28 (S, 6H), 2.60-3.20 (m, 17H), 3.48 (m, 1H), 4.04 (m, 2H), 4.44 (m, 1H), 5.04 (s, 4H), 5.22 (s, 2H), 6.69 (s, 2H), 7.18-7.41 (m, 20H), 8.27 (s, 1H). LRMS ES m/z 912 [MH]$^+$

Preparation 52

(7R)-7-{[N-(tert-butoxycarbonyl)-2,6-dimethyl-L-tyrosyl]amino}-8-oxo-8-[(3-phenylpropyl)amino]octanoic acid

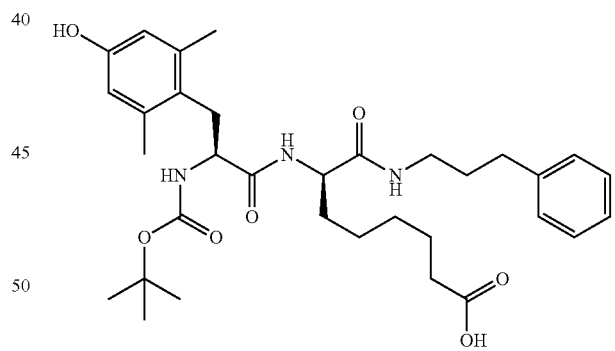

To a solution of methyl (7R)-7-{[N-(tert-butoxycarbonyl)-2,6-dimethyl-L-tyrosyl]amino}-8-oxo-8-[(3-phenylpropyl)amino]octanoic acid (400 mg, 0.65 mmol) from preparation 14 in 3 ml dry THF was added a 0.5M solution of lithium hydroxide in water (3 ml, 1.5 mmol) and the reaction mixture stirred at rt overnight. Volatiles were evaporated and the residue acidified with 0.5M KHSO4. Product was extracted with ethyl acetate and the organic extract washed with brine, dried over MgSO4 and concentrated to a fine white solid which was taken directly into boc deprotection (preparation 28) on basis of LRMS m/z 598 [M+H].

Preparation 53

(2R)-2-(1,3-dioxo-1,3-dihydro-2H-isoindol-2-yl)-4-(methylsulfinyl)butanoic acid

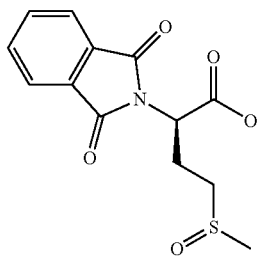 [SMILES: CS(=O)CC[C@H](C(=O)O)N1C(=O)c2ccccc2C1=O]

To a solution of (R)-2-(1,3-dioxoisoindolin-2-yl)-4-(methylthio)butanoic acid (87.124 g, 312 mmol) from preparation 54 in methanol (750 ml) was added hydrogen peroxide (pre-cooled to −30° C.; 38.9 g, 343 mmol) in methanol (250 ml) at −20° C. The reaction mixture was stirred at −20° C. overnight (by use of a cryostat) then warmed to rt over a further 24 hours then to 30° C. for 5 h, LCMS suggesting 95% conversion. The reaction mixture was evaporated under vacuum to give the title compound as a mixture of diastereoisomers that were progressed directly in preparation 3.

Preparation 54

(2R)-2-(1,3-dioxo-1,3-dihydro-2H-isoindol-2-yl)-4-(methylsulfanyl)butanoic acid

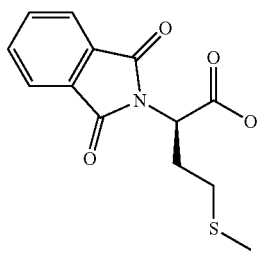 [SMILES: CSCC[C@H](C(=O)O)N1C(=O)c2ccccc2C1=O]

A solution of (R)-2-amino-4-(methylthio)butanoic acid (50 g, 335 mmol), finely ground phthalic anhydride (49.6 g, 335 mmol) and triethylamine (4.67 ml, 33.5 mmol) in toluene (450 ml) was stirred and heated under vigorous reflux in a Dean-Stark apparatus for 2.5 h. Volatiles were evaporated and to the residue was added 600 ml water and 6 ml hydrochloric acid and the mixture stirred vigorously with a mechanical stirrer. After stirring for 30 minutes, the suspension was filtered and filtrate evaporated under vacuum to give the title compound (87.24 g=92% yield).

LC-MS Rt. 1.8 min (>97%). LRMS m/z 280 [M+H].

Preparation 55

N-[N,N'-bis(tert-butoxycarbonyl)carbamimidoyl]-2,6-dimethyl-L-tyrosyl-N-{(2S)-2-[N',N''-bis(tert-butoxycarbonyl)carbamimidamido]-3-phenylpropyl}-N~5~-[N,N'-bis(tert-butoxycarbonyl)carbamimidoyl]-D-ornithinamide

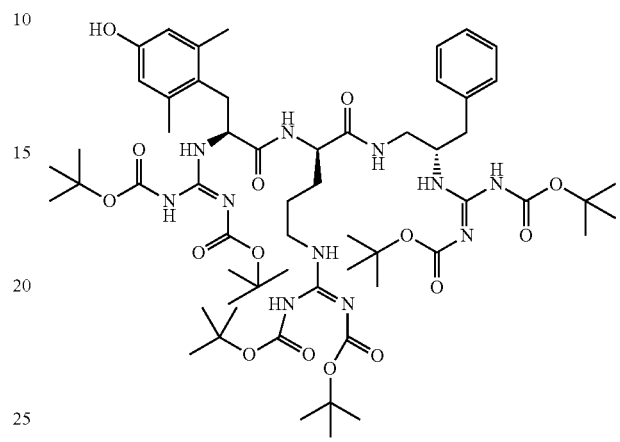

To a solution of Preparation 56 (550 mg, 0.96 mmol) in DCM (4.0 mL) was slowly added TFA (4.0 mL) at 0° C. The mixture was stirred for 30 minutes at 0° C. and RT for further 3 hours then concentrated to a fluffy powder. To a suspension of this crude material in DCM (6.0 mL) were added TEA (0.97 g, 9.6 mmol) and tert-butyl {N-(tert-butoxycarbonyl)-N'-[(trifluoromethyl)sulfonyl]carbamimidoyl}carbamate (1.5 g, 3.9 mmol). The resultant clear solution was stirred at room temperature overnight, quenched with saturated NaHCO₃ aq., extracted with EtOAc, dried over MgSO₄, concentrated and purified by column chromatography (80 g silica gel, eluant heptanes:EtOAc 4:1 to 1:1) to give a white powder (410 mg).

$^1$H NMR (400 MHz, CDCl₃) δ: 0.91-1.10 (m, 2H), 1.31-1.39 (m, 1H), 1.45-1.6 (m, 45H), 2.33 (s, 6H), 2.73-2.90 (m, 2H), 3.01 (ap t, 1H), 3.10-3.25 (m, 2H), 3.28-35 (m, 1H), 3.43 (dd, 1H), 4.20-4.25 (m, 1H), 4.28-4.35 (m, 1H), 4.65-4.75 (m, 1H) 5.76 (d, 1H), 6.58 (s, 2H), 7.17-7.22 (m, 3H), 7.24-7.29 (m, 2H), 8.21 (ap t, 1H), 8.34 (ap t, 1H), 8.50 (d, 1H), 8.95 (d, 1H).

LRMS ES+ m/z: 591 [M+2H]²⁺

Preparation 56

N-(tert-butoxycarbonyl)-2,6-dimethyl-L-tyrosyl-N-[(2S)-2-amino-3-phenylpropyl]-D-ornithinamide

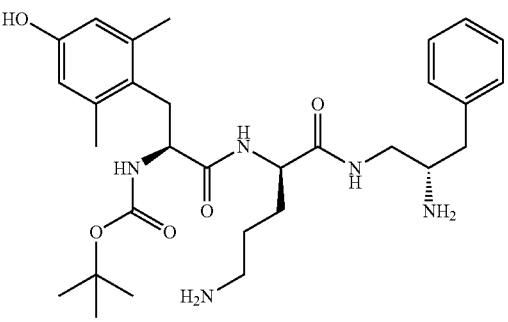 [SMILES: Cc1cc(O)cc(C)c1C[C@H](NC(=O)OC(C)(C)C)C(=O)N[C@H](CCCN)C(=O)NC[C@@H](N)Cc1ccccc1]

The title compound was prepared from the product of Preparation 57 (1.95 g) in MeOH (24 mL) to which was added ammonium formate (0.75 g, 12 mmol) and palladium hydroxide on carbon (20 w/w %, 83 mg, 0.12 mmol) at room temperature. The mixture was warmed to 6000 for 3 hours, filtered through Arbocel, concentrated and used without further purification.

$^1$H NMR (400 MHz, d6-DMSO) δ: 0.87-1.00 (m, 2H), 1.11-1.25 (m, 1H), 1.30 (s, 9H), 1.53-1.66 (m, 1H), 2.14 (s, 6H), 2.28-2.45 (m, 4H), 2.59-2.69 (m, 2H), 2.83-2.99 (m, 3H), 3.91-4.04 (m, 2H), 6.34 (s, 2H), 7.03 (d, 1H), 7.13-7.20 (m, 3H), 7.22-7.27 (m, 2H), 7.63-7.71 (m, 1H), 7.91-7.96 (m, 1H)

LRMS ES+ m/z: 556 [M+H]$^+$

Preparation 57 benzyl {(4R)-5-{[(2S)-2-{[(benzyloxy)carbonyl]amino}-3-phenylpropyl]amino}-4-[(tert-butoxycarbonyl)amino]-5-oxopentyl}carbamate

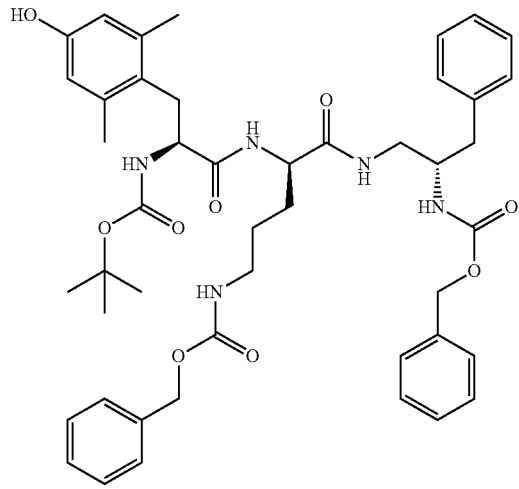 [SMILES: Cc1cc(O)cc(C)c1C[C@H](NC(=O)OC(C)(C)C)C(=O)N[C@H](CCCNC(=O)OCc1ccccc1)C(=O)NC[C@H](Cc1ccccc1)NC(=O)OCc1ccccc1]

The title compound was made using the procedure of Preparation 2 using N-[3-(dimethylamino)propyl]-N'-ethylcarbodiimide hydrochloride, N-(tert-butoxycarbonyl)-2,6-dimethyl-L-tyrosine and the product of Preparation 58 (1.41 g) to afford a crude white powder (1.95 g) which was used without further purification.

$^1$H NMR (400 MHz, CDCl$_3$) δ: 0.85-0.99 (m, 2H), 1.11-1.25 (m, 1H), 1.31 (s, 9H), 1.35-1.51 (m, 1H), 2.23 (s, 6H), 2.63-2.72 (m, 1H), 2.80-3.15 (m, 4H), 3.40-3.49 (m, 1H), 3.85-4.12 (m, 2H) 4.18-4.23 (m, 1H), 4.85-5.18 (m, 4H), 5.21-5.33 (m, 2H), 5.69 (d, 1H), 6.44 (s, 2H), 7.11-7.43 (m, 15H)

LRMS ES+ m/z: 824 [M+H]$^+$

Preparation 58 benzyl [(4R)-4-amino-5-{[(2S)-2-{[(benzyloxy)carbonyl]amino}-3-phenylpropyl]amino}-5-oxopentyl]carbamate

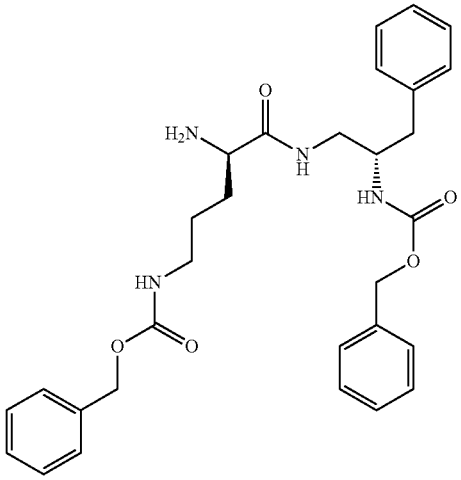 [SMILES: N[C@H](CCCNC(=O)OCc1ccccc1)C(=O)NC[C@H](Cc1ccccc1)NC(=O)OCc1ccccc1]

The title compound was prepared using the method of Example 10 and the product of Preparation 59 (1.668 g) to afford a white powder (1.41 g) which was used without further purification.

$^1$H NMR (400 MHz, d6-DMSO) δ: 1.28-1.61 (m, 4H), 2.60 (dd, 1H), 2.72 (dd, 1H), 2.95 (dd, 2H), 3.10 (dd, 2H), 3.22 (dd, 1H), 3.69-3.78 (m, 1H), 4.88-5.02 (m, 4H), 7.13-7.37 (m, 15H)

LRMS ES+ m/z: 533 [M+H]$^+$

Preparation 59 benzyl {(4R)-5-{[(2S)-2-{[(benzyloxy)carbonyl]amino}-3-phenylpropyl]amino}-4-[(tert-butoxycarbonyl)amino]-5-oxopentyl}carbamate

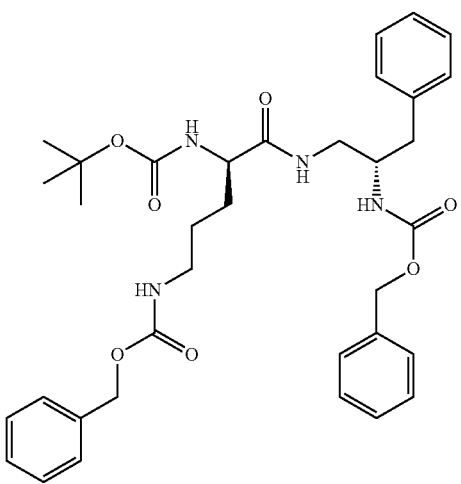 [SMILES: CC(C)(C)OC(=O)N[C@H](CCCNC(=O)OCc1ccccc1)C(=O)NC[C@H](Cc1ccccc1)NC(=O)OCc1ccccc1]

The title compound was made following the method of preparation 2 using N~5~-[(benzyloxy)carbonyl]-N~2~-(tert-butoxycarbonyl)-D-ornithine (970 mg) and benzyl [(2S)-1-amino-3-phenylpropan-2-yl]carbamate (851 mg) to give a white powder (1.85 g) which was used without further purification.

$^1$H NMR (400 MHz, CDCl$_3$) δ: 1.31-1.75 (m, 4H), 1.41 (s, 9H), 2.70-2.84 (m, 2H), 3.08-3.50 (m, 4H), 3.92-3.99 (m, 1H), 4.06-4.11 (m, 1H), 4.95-5.09 (m, 4H), 5.13-5.21 (m, 1H), 5.28-5.32 (m, 1H), 5.43-5.50 (m, 1H), 6.99 (m, 1H), 7.13-7.36 (m, 15H)

LRMS ES+ m/z: 633 [M+H]$^+$

Biological Activity

Beta-Arrestin Assay

The ability of agonists to cause recruitment of beta-arrestin to the mu opioid receptor was measured using DiscoveRx PathHunter technology. A pro-linked tagged mu-opioid receptor and an EA-tagged beta-arrestin were expressed in U20S cells and beta-arrestin recruitment measured following the methodology in McGuinness et al., 2009 (J Biomol Screen 14:49-58, Characterizing cannabinoid CB2 receptor ligands using DiscoverRx PathHunter beta-arrestin assay—McGuinness D., Malikzay A., Visconti R., Lin K., Bayne M., Monsma F., Lunn C A.)

Data appear in the Table below under "arrestin EC$_{50}$" in nM.

Forskolin Stimulated cAMP

The ability of mu opioid receptor agonists to inhibit forskolin stimulated cAMP production was measured in CHO cells recombinantly expressing the mu opioid receptor, using alphascreen technology as described in Nickolls et al., 2005, with the additional inclusion of 50 uM forskolin in the assay buffer. (J Pharmacol Exp Ther 313; 1281-88, Functional selectivity of melanocortin 4 receptor peptide and non-peptide agonists: Evidence for ligand specific conformational states. Nickolls S A., Fleck B., Hoare S., Maki R.)

Data appear in the Table below under "mu-opioid IC$_{50}$" in nM.

Functional Mu-Opioid Activity (GPI)

Functional activity at the mu-opioid receptors was determined using the electrically stimulated guinea pig isolated myenteric plexus preparation following the methodology of Hughes, J.; Kosterlitz, H. W. and Leslie, F. M. Br. J. Pharmacol. 1975, 53, 371.

Data appear in the Table below under "GPI IC$_{50}$" in nM.

Metabolic Stability

In vitro measurement of substrate metabolism can be determined using the microsomal cytochrome P450 mono-oxygenase system. This is a useful application in ranking clearance of a number of compounds by Phase I (including cytochrome P450) metabolism prior to in vivo assessment Measurement of intrinsic clearance using these methods also allows a comparison of species difference to be made to assist with translation of pharmacokinetic parameters from preclinical to clinical study.

Rat and Human Liver Microsomal Stability Assay (RLM and HLM Respectively)

Human and rat Liver microsomal assays were performed using pooled microsomes from the Pfizer Global Supply (BD Gentest™). Chemical reagents were purchased from commercial sources (Sigma-Aldrich) and drug entities synthesised at Pfizer Global Research. Incubation mixtures contained 50 mM phosphate buffer pH 7.4, 5 mM MgCl$_2$, 5 mM isocitric acid and 1 unit/ml isocitric dehydrogenase. The microsomes were defrosted at room temperature and sufficient volumes added to give a final concentration of 0.5 nmol cytochrome P450/ml. Following the addition of 1 μM of substrate, the incubation was pre-incubated at 37° C. for 5 minutes. The reaction was then initiated by the addition of 1 mM NADP and incubation aliquots are taken over a 1 h time course. The reaction was subsequently stopped by addition of acetonitrile cooled on ice. The incubation mixture was then centrifuged and the supernatant removed for injection onto LC-MS/MS system. Providing that the substrate concentration is below the Km, the metabolism should be first order giving a log-linear plot of substrate disappearance over time. The gradient of this line is the first order rate constant (k) and this maybe converted to estimate a substrates intrinsic clearance when factoring in the protein concentration.

The intrinsic clearance in rat or human liver microsomes is calculated from:

$$Cl_{int}(\text{ul/min/mg protein}) = \frac{k \times \text{incubation volume}}{\text{Protein concentration}}$$

Where, k=−slope of Ln concentration vs. time (min−1)

Lipophilicity (LogD)

LogD octanol (pH 7.4) is a measure of lipophilicity that accounts for both hydrophobic and hydrogen-bonding interactions of a given substrate. This assay is based on shake-flask methodology, performed in a fully automated manner in a 0.1M phosphate buffer pH7.4—octanol system. Three positive controls (propranolol (log D=1.1±0.2), midazolam (log D=3.3±0.2). and amitriptyline (log D=2.7±0.2) are run with each assay.

After addition of the test substance in DMSO stock solution to the mixture and vigorous agitation followed by separation of the octanol and buffer layers by centrifugation, duplicate samples are removed from each layer and diluted prior to analysis by LC-MS/MS. Peak area is corrected for dilutions and the following equation used to calculate the log D (pH 7.4):

$$\text{Mean } LogD = \text{Mean } \log_{10} \frac{(\text{corrected peak area for octanol sample})}{(\text{corrected peak area for buffer sample})}$$

The duplicate log D values must be with 0.4 log units of each other and the positive controls must be within 0.2 log units of the known log D value.

| | | | Data | | | |
|---|---|---|---|---|---|---|
| EXAMPLE NO | GPI IC$_{50}$ (nM) | β-Arrestin EC$_{50}$ (nM) | mu-opioid IC$_{50}$ (nM) | HLM clearance (μL/min/mg) | RLMclearance (μL/min/mg) | LOGD |
| 1 | 1.25 | 41.4 | 26 | 10.6 | 8.5 | −0.2 |
| 2 | 3.84 | 34.8 | | 15.9 | 8.5 | −0.7 |
| 3 | 55.5 | 10000 | | | | |

-continued

| EXAMPLE NO | GPI IC$_{50}$ (nM) | β-Arrestin EC$_{50}$ (nM) | mu-opioid IC$_{50}$ (nM) | HLM clearance (μL/min/mg) | RLMclearance (μL/min/mg) | LOGD |
|---|---|---|---|---|---|---|
| 4 | 91.4 | 5070 | | 9.54 | 13.4 | −0.3 |
| 5 | 3.67 | 47.6 | | | | |
| 6 | 6.94 | 162 | | 8 | 8.5 | |
| 7 | 2.65 | 2460 | 116 | 8.61 | 9.48 | 0.8 |
| 8 | 5 | | 26.6 | 15.4 | 12.1 | −0.35 |
| 9 | 1.96 | 55.2 | 15.3 | 13.6 | 12.9 | |
| 10 | 1.27 | 17.6 | | | | |
| 11 | 4.6 | | 8.59 | 74 | 61 | −0.1 |
| 12 | 1.89 | | | | | |

All publications cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention.

Accordingly, the invention is limited only by the following claims.

The invention claimed is:

1. A compound of formula INT1

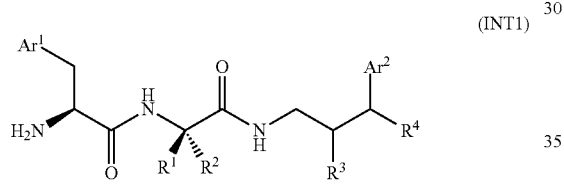

(INT1)

whereby $Ar^1$ is phenyl substituted by two or more substituents independently selected from OH, $C_{1-3}$ alkyl and halogen, or $Ar^1$ is phenyl fused to a 5- or 6-membered heterocycle optionally substituted by one or more substituents independently selected from halogen, OH and =O, $Ar^2$ is phenyl optionally substituted by one or more substituents independently selected from OH, $C_{1-3}$ alkyl and halogen, or $Ar^2$ is phenyl fused to a 5- or 6-membered heterocycle optionally substituted by one or more substituents independently selected from halogen, OH, and =O, Gu is guanidinyl (or a tautomeric form thereof) optionally substituted by up to 4 substituents independently selected from $C_{1-3}$ alkyl, $R^1$ is independently H or $C_{1-5}$ alkyl optionally substituted by Y, where Y is halogen, $S(O)_m$—($C_{1-3}$ alkyl), $CO_2$—$R^5$ or Gu, where $R^5$ is H or $C_{1-6}$ alkyl, and m is 0, 1 or 2, $R^2$ is independently H or $C_{1-3}$ alkyl, or $R^1$ and $R^2$ together with the carbon atom to which they are attached can be a cyclopropyl group, one of $R^3$ and $R^4$ is H and the other is Q where Q is $NH_2$, $NHC(O)(C_{1-6}$ alkyl), Gu, $NHC(O)(CH_2)_nNH_2$, $NHC(O)(CH_2)_nGu$, or $(CH_2)_nGu$, where n is 1, 2, 3, 4 or 5, or a tautomer thereof.

2. A pharmaceutical composition comprising a compound of the formula (INT1) or a pharmaceutically acceptable salt thereof, according to claim 1, and a pharmaceutically acceptable carrier.

3. A method of treatment of pain associated with opioid receptor in a mammal, comprising treating said mammal with an effective amount of a compound of the formula (INT1) or a pharmaceutically acceptable salt thereof, according to claim 1.

* * * * *